United States Patent [19]
Maierhofer et al.

[11] Patent Number: 5,853,753
[45] Date of Patent: Dec. 29, 1998

[54] LIPOSOMES, METHOD OF PREPARING THE SAME AND USE THEREOF IN THE PREPARATION OF DRUGS

[75] Inventors: Günther Maierhofer, Munich; Paul Höfer, Dietersheim; Oswald Rottmann, Freising, all of Germany

[73] Assignee: Dianorm G. Maierhofer GmbH, Munich, Germany

[21] Appl. No.: 800,802

[22] Filed: Feb. 18, 1997

Related U.S. Application Data

[63] Continuation of Ser. No. 367,128, filed as PCT/EP93/01545 Jun. 7, 1993, abandoned.

[30] Foreign Application Priority Data

Jul. 8, 1992 [DE] Germany .............................. 42 2 447.0
Sep. 25, 1992 [DE] Germany .......................... 42 32 231.6

[51] Int. Cl.$^6$ .......................... A61K 9/127; A61K 9/133
[52] U.S. Cl. ......................................................... 424/450
[58] Field of Search ........................ 424/400; 428/402.2; 436/829

[56] References Cited

U.S. PATENT DOCUMENTS 4,731,210  3/1988  Weder ...................................... 264/4.3

FOREIGN PATENT DOCUMENTS 0056781  7/1982  European Pat. Off. .
0475160  3/1992  European Pat. Off. .

OTHER PUBLICATIONS

Baugham BBA 511, pp. 388–396, 1978.

*Primary Examiner*—Gollamudi S. Kishore
*Attorney, Agent, or Firm*—Sughrue, Mion, Zinn, Macpeak & Seas, PLLC

[57] ABSTRACT

The present invention relates to liposomes which can be obtained by mixing bilayer-forming lipids containing, at least in part, unsaturated fatty-acid chains, with an aqueous solution of bile acid and/or at least one derivative thereof and supplying mechanical energy, wherein before mixing, the lipids are present either as such or dissolved in water-miscible solvent. The invention further relates to a method of preparing such liposomes and their use in the preparation of drugs.

10 Claims, 10 Drawing Sheets

FIG. 1A
| INH. PERI. PLA. NO. % OF CONTR. | | CONTROLS PLAQUE NO. % OF CONTROL | |
|---|---|---|---|
| 30 MIN 3 PLAQUES <1% | 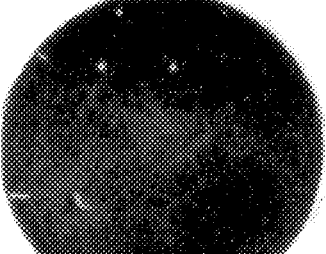 | | |
| 10 MIN 108 PLAQUES 26% | 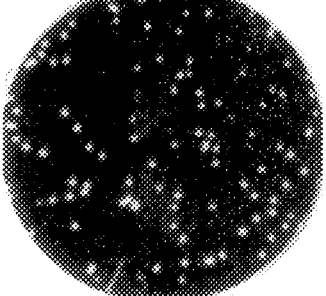 | | |
| 5 MIN 170 PLAQUES 43% | 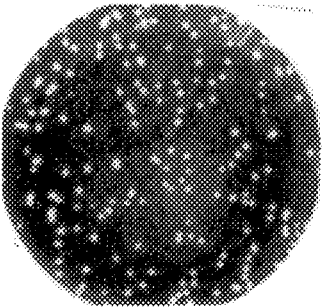 | | |
| 2 MIN 183 PLAQUES 44% | 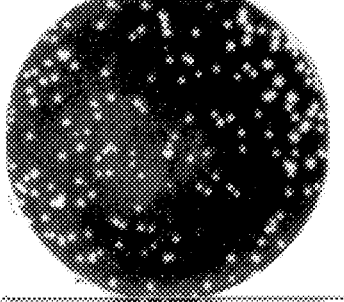 | CELL CONTROL 0 PLAQUES 0% | 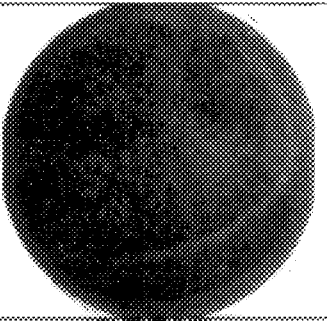 |
| 0.5 MIN 197 PLAQUES 47% | 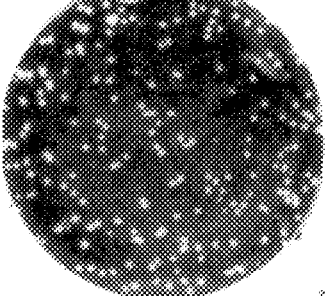 | VIRUS CONTROL 420 PLAQUES 100% | 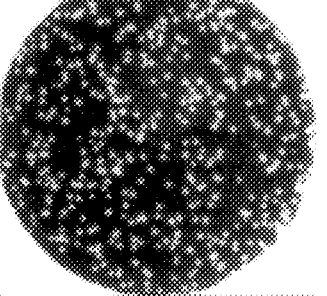 |

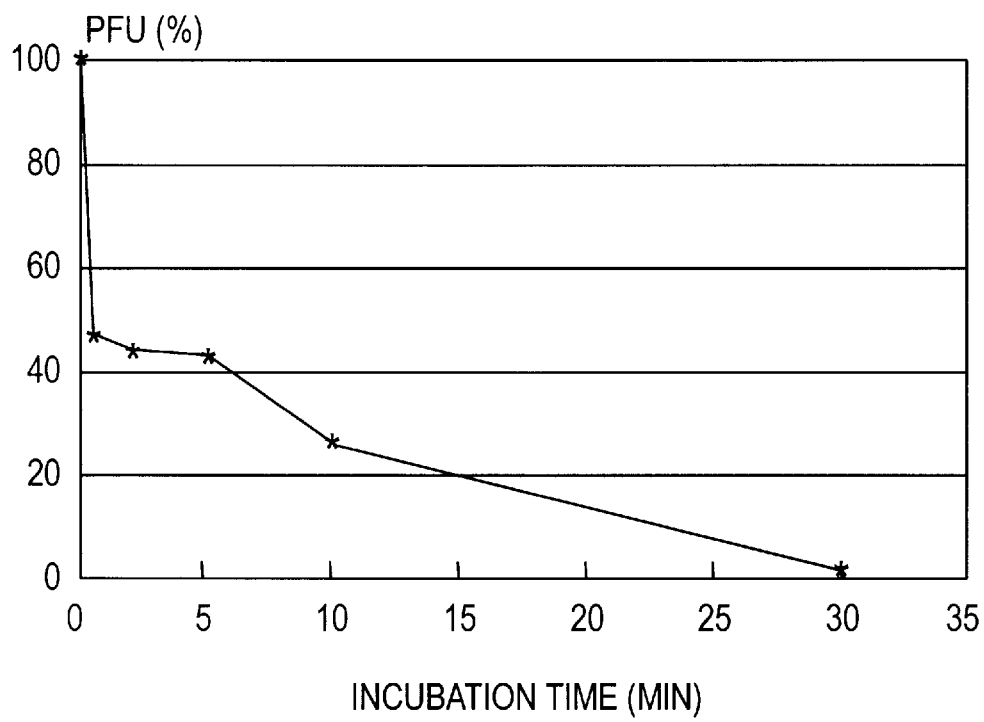

FIG. 2A
| LIP. CONCENTR. PLAQUE NO. % OF THE CONTR. | | CONTROLS PLAQUE NO. % OF THE CONTROL | |
|---|---|---|---|
| $7.3 \times 10^{13}$ LIPOSOMES/ml 30 PLAQUES 21% | 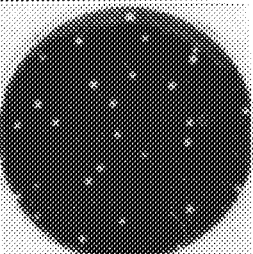 | | |
| $3.7 \times 10^{13}$ LIPOSOMES/ml 42 PLAQUES 30% | 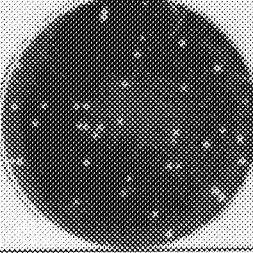 | | |
| $7.3 \times 10^{12}$ LIPOSOMES/ml 76 PLAQUES 54% | 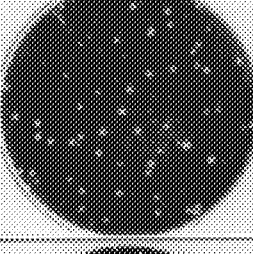 | | |
| $3.7 \times 10^{12}$ LIPOSOMES/ml 90 PLAQUES 64% | 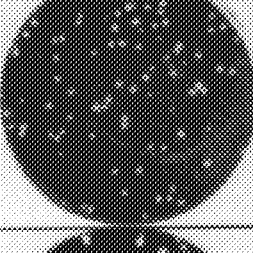 | | |
| $7.3 \times 10^{11}$ LIPOSOMES/ml 99 PLAQUES 70% | 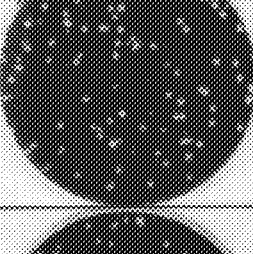 | | |
| $3.7 \times 10^{11}$ LIPOSOMES/ml 93 PLAQUES 66% | 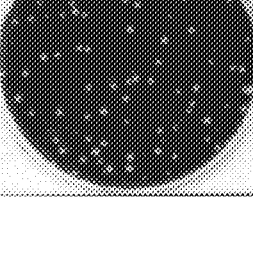 | VIRUS CONTROL 141 PLAQUES 100% | 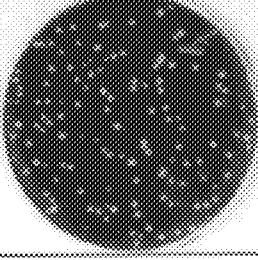 |

FIG. 3
| VIR. + LIPOS. VIR. DILUTION PLAQUE NO. | | VIR. CONTR. VIR. DIL. PLAQUE NO. | |
|---|---|---|---|
| VIRUS DILUTION $10^{-5}$ 1 PLAQUE | 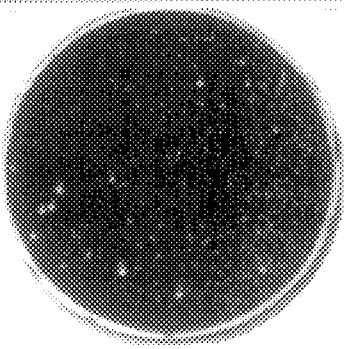 | VIRUS DILUTION $10^{-5}$ 14 PLAQUES | 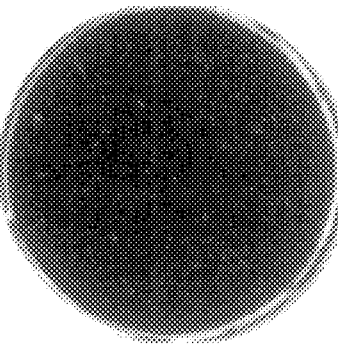 |
| VIRUS DILUTION $10^{-4}$ 3 PLAQUES | 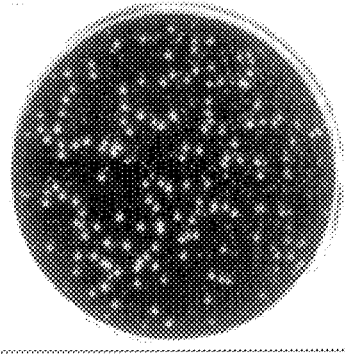 | VIRUS DILUTION $10^{-4}$ 170 PLAQUES | 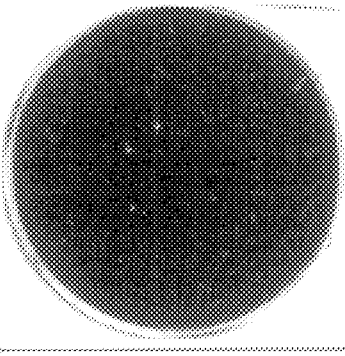 |
| VIRUS DILUTION $10^{-3}$ 101 PLAQUES | 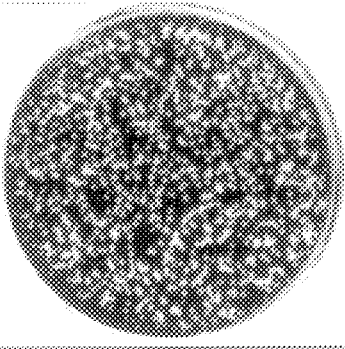 | VIRUS DILUTION $10^{-3}$ >500 PLAQUES | 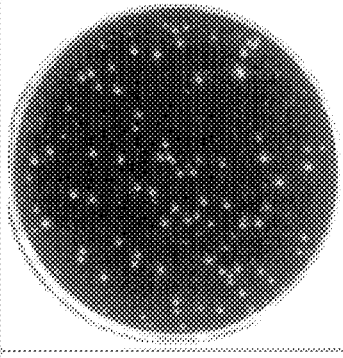 |
| VIRUS DILUTION $10^{-2}$ >500 PLAQUES | 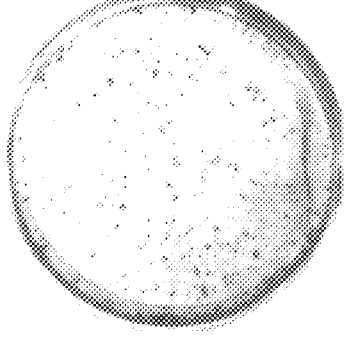 | VIRUS DILUTION $10^{-2}$ >>500 PLAQUES | 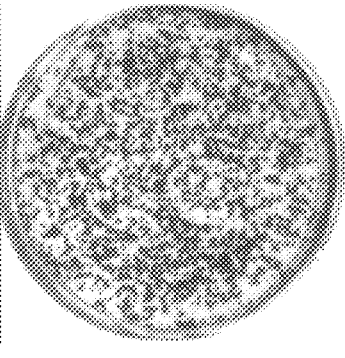 |

PARTICLE DIAMETER
DIFFERENTIAL WEIGHT (SIZE DISTRIBUTION PROCESSOR)

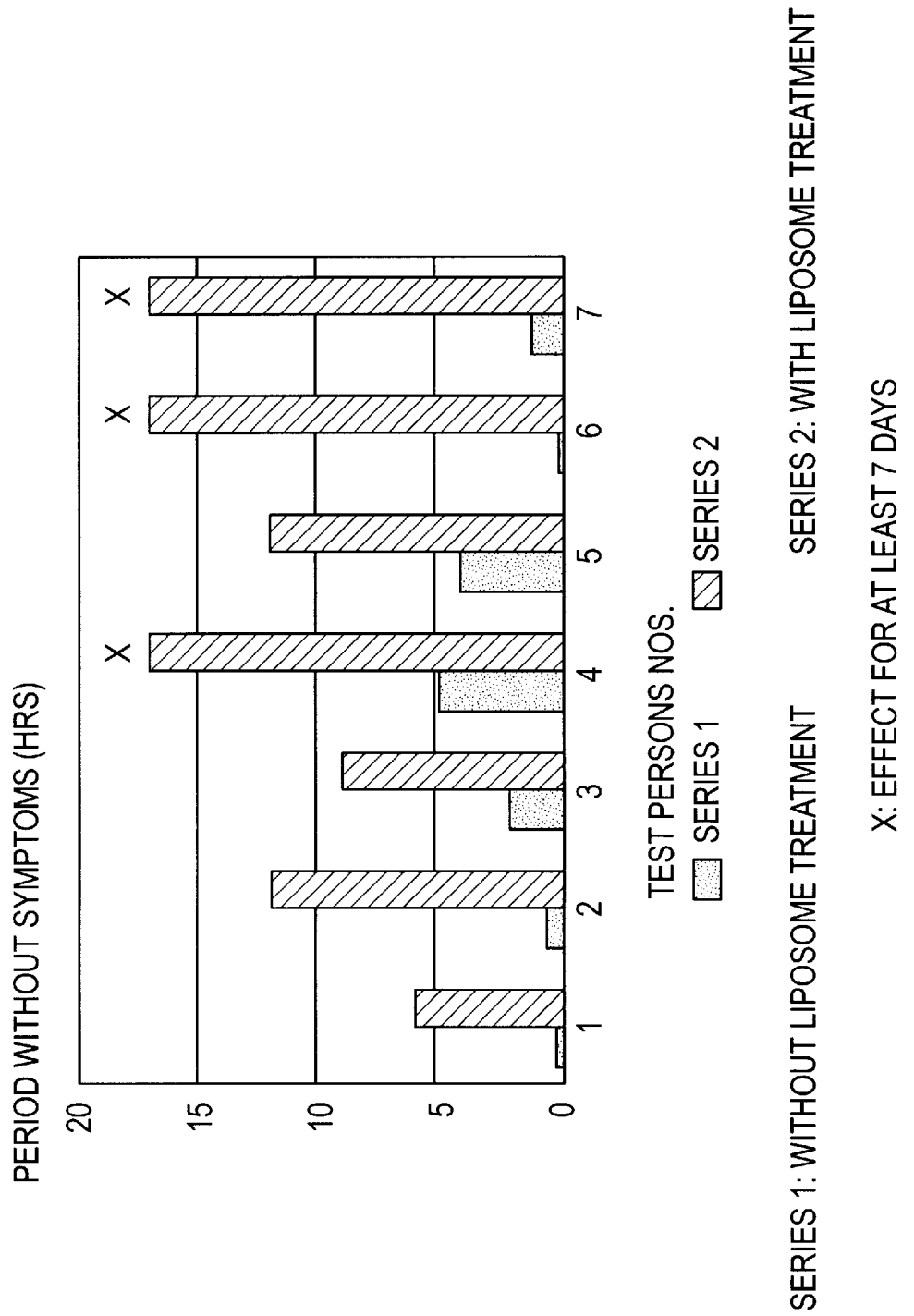

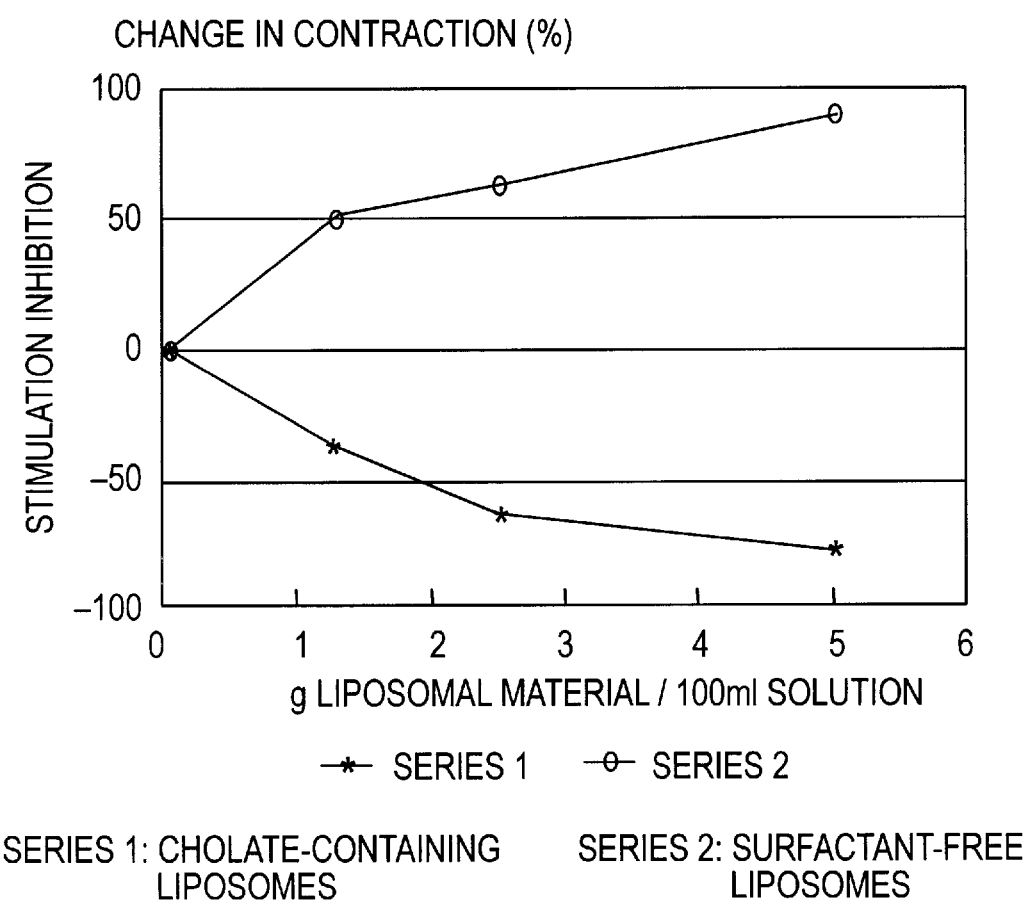

LIPOSOMES, METHOD OF PREPARING THE SAME AND USE THEREOF IN THE PREPARATION OF DRUGS

This is a Continuation of application Ser. No. 08/367,128 filed Jan. 6, 1995 now abn., and a 371 of PCT/EP93/01545 filed Jun. 17, 1993.

The present invention relates to liposomes, a method of preparing liposomes and the use of liposomes for preparing drugs.

Liposomes are spherical aqueous compartments that are surrounded by at least one fully closed lipid bilayer and may have a diameter of from 20 nm to several 1000 nm. Because of their membrane structure, which is comparable with the structure of a cell membrane, they often serve as model systems for examining membrane properties in vitro. In the last few years they have gained more and more importance as vehicles for transporting pharmaceutical and cosmetic agents, as they are capable of enclosing hydrophilic agents in the aqueous compartment or can integrate hydrophobic agents into the liposome membrane on account of their structure.

Methods for preparing liposomes are already known in the prior art. Methods of preparing liposomal drugs are also known. For instance, EP-A-56781 describes a method for preparing liposomal drugs wherein associates which are formed from lipid and a surfactant and are present in an aqueous phase are converted into liposomes by withdrawing the surfactant. The addition of medicinal substances or pharmaceutical agents prior to the withdrawal of the surfactant leads to the incorporation of said agents into the liposomes. The molar ratio of lipid-bilayer forming agent and surfactant is specified to be 0.1 to 2.

EP-A-220797 describes the preparation of liposomes from phospholipid and hydrophilic nonionic surfactants. In the presence of active substances during the liposome formation, these are incorporated into the liposomes.

EP-A-130577 describes the production of liposomes by mixing lipid and a water-soluble non-volatile solvent and by dispersing the solution in water. A pharmaceutical agent can be enclosed in the liposomes by mixing the organic solvent containing the membrane components, with an aqueous medium containing the drugs.

The prior-art liposomes have in common that in the final analysis all of them are conceived as vehicles for pharmaceutical agents which are either enclosed in the aqueous compartment of the liposome or integrated into the membrane.

It is now the object of the present invention to provide novel liposomes.

According to the invention this object is attained by liposomes which can be obtained by a) mixing bilayer-forming lipids containing, at least in part, unsaturated fatty-acid chains, with an aqueous solution of bile acid and/or at least one of the derivatives thereof, wherein before mixing the lipids are present either as such or are dissolved in a water-miscible solvent, and by b) supplying mechanical energy.

Surprisingly enough, it has been found that the liposomes of the invention are suited for the prophylactic or therapeutic treatment of a multitude of diseases although they do not contain any pharmaceutical or cosmetic agents. These properties of the liposomes that are entirely unexpected and will be explained in more detail further below are due to the new composition of the liposomes of the invention, i.e. their structure of bilayer-forming lipids comprising, at least in part, unsaturated fatty-acid chains in combination with bile acid and/or bile acid derivatives.

In accordance with the invention, the lipids and/or bile acid derivatives are preferably physiologically tolerated compounds, preferably naturally occurring compounds. Bile acid itself can., e.g., be found physiologically in the form of its conjugates with glycine or taurine as bile component, and it is also contained in blood in a concentration of from 1 to 2 mg per 100 ml.

The term "lipid", as is used here, shall cover lipoids, i.e. lipoid-like substances, such as carotinoids, amides (such as ceramides) and more complex compounds, such as glycolipids, e.g. cerebrosides and gangliosides, apart from classical lipids having, at least in part, unsaturated fatty-acid chains. Finally, the term also covers phospholipids, such as sphingomyelins, lecithins, cephalins and cardiolipins. Preferred lipids are phospholipids, sphingolipids, and glycolipids. Especially preferred compounds comprise cerebrosides and ceramides, naturally occurring phosphocholines, phosphatidic acids or phosphatidyl glycerins, and optionally lysophospholipids. Preferred lipids have a phase transition temperature of less than 37° C., especially preferably less than 25°.

Apart from the bilayer-forming lipids, the liposomes of the invention may also contain lipids which are not bilayer-forming agents. Examples thereof are cholesterols, sulfatides, phosphatidylinosites, and phosphatidylinosite phosphates. In an especially preferred embodiment, natural lipid preparations are used for preparing liposomes. Most of the time, these contain lipids, depending on the degree of purity, with the lipids being uncapable of forming bilayers.

The lipids are used for preparing the liposomes either as such or in a water-miscible solvent. The water-miscible solvent is, for instance, at least an alcohol having 1 to 6 carbon atoms. Ethanol is used in a preferred embodiment.

The concentration of the lipids in the mixture with an aqueous solution of bile acid and/or at least one of the derivatives thereof is 0.625 mmole/l to 187.5 mmole/l, preferably 37.5 to 150 mmole/l, and especially preferably 62.5 to 125.0 mmole/l.

The proportion of unsaturated fatty-acid chains of the bilayer-forming lipids used for the preparation of the liposomes of the invention is at least 4 wt. %, for instance in the case of impure lecithins, preferably 40 to 80 wt. %, based on the total lipid content, for instance in the case of pure to highly pure lecithins. Preferred unsaturated fatty-acid chains are palmitoleic, oleic, linoleic, linolenic or arachidonic acid.

The concentration of the bile acid and/or the derivatives thereof depends on the concentration of the lipids. The molar ratio of lipid to bile acid and/or bile acid derivative (L:G) is preferably 2 to 20, preferably 2.7 to 6.7, and especially preferably 3.1 to 5.5.

Every bile acid derivative can be used according to the invention. Preferred bile acid derivatives are sodium cholate, sodium deoxycholate, sodium glycocholate, sodium taurocholate, sodium taurodeoxycholate, sodium ursocholate, and sodium chenoxycholate. The added bile acid and/or the derivatives thereof lead to a decrease in the surface tension of the liposomes and thus to an increased fusogenity which facilitates the fusion of the liposomes with body cells. It is also assumed that a presumably slight change in membrane potential which is more or less limited in time takes place on account of an interaction between surface tension and membrane potential after fusion of the liposomes with cells. For instance, Olson et al. (10) write that a weak depolarization of the transmembrane potential will take place a few minutes after rat liver cells have been treated with taurocholate. Furthermore, it might be that the membrane components, depending on their spatial arrangement, are subjected to certain spatial changes by the bile acid or the derivatives thereof, the changes being expressed in a changed permeability of the membrane or a changed production rate for "second messenger". The surfactant contained in the liposome must, however, not lead to a destabilization of either the liposome membrane, or, after fusion, of the cell membrane. Among all of the tested surfactants, bile acid and the derivatives thereof fulfill these requirements best. Moreover, it has been observed that the liposomes prepared in this way have been very stable for long periods of time.

To be suited for the prophylactic or therapeutic uses as described below, the liposomes according to the invention need not contain any pharmaceutically or cosmetically active agents apart from the above-mentioned liposome components. They are therefore also designated as "physiological liposomes" in the following description. In accordance with the invention, however, the liposomes may also contain one or more physiologically tolerated additions selected from the group consisting of provitamins, vitamins, mineral substances, oils, antibiotics, carbohydrates, proteins, oligopeptides, amino acids and reducing agents. These additions, as well as all of the other additions mentioned in the description, may be added to the mixture containing the liposome components, either together with the lipid or the surfactant, or also separately.

In a preferred embodiment, the liposomes of the invention contain at least one provitamin, such as β-carotine or ergosterol, and/or vitamin or derivatives thereof, preferably selected from the group consisting of the vitamins A, B, C, D, and E. Said provitamins or vitamins are preferably used in the following concentrations: β-carotine: 0.01 to 0.15 wt. %, ergosterol: 0.001 to 0.1 wt. %, vitamin A: 0.05 to 1 wt. %, especially preferred is 0.1 to 0.3 wt. %, vitamins B1, B2, B6 and nicotinamide: 0.05 to 0.5 wt. %, especially preferred is 0.1 to 0.3 wt. %, vitamin B12: 0.0001 to 0.001 wt. %, folic acid and biotin: 0.0005 to 0.002 wt. %, pantothenate: 0.5 to 2.5 wt. %, especially preferred is 0.1 to 0.3 wt. %, vitamin C: 0.1 to 30 wt. %, especially preferred are 4 to 12 wt. %, vitamin D: 0.01 to 0.5 wt. %, and vitamin E: 0.01 to 0.2 wt. %, especially preferred is 0.2 to 1 wt. %.

Should the liposomes contain a mineral substance, the latter will preferably contain at least one of the elements Li, Na, K, Mg, Ca or Fe, preferably in salt form as a fluoride, chloride, sulfite, sulfate or phosphate. The concentration of the mineral substances is preferably 0.01 wt. % to 4 wt. %, especially preferred is 0.1 to 1 wt. %.

In another embodiment the liposomes of the invention may contain one or more oils. Preferably, they contain at least one pharmaceutical oil of vegetable or animal origin; especially preferred oils are here selected from the group consisting of jojoba oil, borage oil, evening primrose oil, chamonile oil, tea tree oil or fish oil. The concentration of the oils is preferably from 0.01 wt. % to 4 wt. %, especially preferred is 0.1 wt. % to 2 wt. %.

Preferred carbohydrates are ribose, arabinose, glucose, mannose, galactose, fructose, sorbose, saccharose, lactose, maltose and optionally also mucopolysaccharides. These carbohydrates may, e.g., be used in a concentration of from 0.05 to 2 wt. %.

Preferred amino acids are essential amino acids, i.e., isoleucine, leucine, lysine, methionine, phenylalanine, theronine, tryptophane, and valine, also arginine, histidine, cysteine and tyrosine. These amino acids and also citric and pyruvic acids are preferably used in a concentration of from 0.001 to 0.2 wt. %.

In another preferred embodiment, at least one antioxidant is added to the liposomes of the invention, preferably at least one physiologically tolerated antioxidant. The antioxidants are preferably BHA, BHT, octyl or dodecyl gallate, $SO_2$, for instance in the form of sodium sulfites or sodium thiosulfite, lactic acid, citric acid, tartaric acid and/or the salts thereof, vitamin C, vitamin E and uric acid and the salts thereof. Especially preferred, physiologically tolerated antioxidants are α-tocopherol, bilirubin, vitamin C, vitamin E, uric acid, and the salts and/or derivatives thereof. Uric acid and the salts thereof are preferably added in a concentration of 0.01 to 1 wt. %, vitamin C in a concentration of 0.01 to 2 wt. %, and vitamin E in a concentration of 0.01 to 0.1 wt. %.

The liposomes according to the invention may also contain one or more conventional adjuvants and/or additives, if necessary, preferably gel-forming agents, buffer substances, membrane stabilizers and preservatives.

The gel-forming agents serve to thicken formulations; thickening agents, such as collagen and/or hyaluronic acid, may here be added in a concentration of preferably 0.01 to 0.2 wt. %, likewise organic hydrogel-forming agents, such as methyl cellulose, hydroxyethyl cellulose, carboxymethylcellulose, starch or alginate, which may form a film in a concentration of from 1 to 6 wt. % or may have a penetrating effect in the preferably used concentration of from 0.01 to 2 wt. %, especially preferred is 0.01 to 0.5 wt. %, for instance, polyacrylates (Carbopol®, Hostacerin®, Rhodigel®, Hispagel®, or Xanthan Gum, etc.).

The buffer substances are added to guarantee a desired pH over long storage periods. Their absolute concentration will therefore always follow from the desired pH value. For instance, citrate buffer, acetate buffer, phosphate buffer and/or citric acid buffer is/are normally used, or one of the known buffer solutions for biological media, for instance tris buffer or trismaleate buffer.

Substances added for other reasons may have a membrane-stabilizing effect, the membrane stabilization thereof being a side effect, for instance mineral substances in salt form, buffer substances, antioxidants and bile acid and the derivatives thereof. Furthermore, cholesterol may also be added in a concentration of from 0.1 to 1% and also glycerin, glycol or polyethylene glycol in a concentration of 0.1 to 10%, preferably 1 to 5%.

The preservatives used may be formic acid in a concentration of preferably 0.03 to 0.4 wt. %, acetic acid (preferably 0.3 to 3 wt. %), propionic acid, lactic acid and sorbic acid in a concentration of preferably 0.05 to 6 wt. %, especially preferred is 0.05 to 12 wt. %, $SO_2$ (preferably 0.01 to 0.6 wt. %), salicylic acid and the salts thereof (preferably 0.01 to 0.5 wt. %), PBH ester (preferably 0.05 to 0.6 wt. %), imidazolidinyl urea derivatives (preferably 0.01 to 0.6 wt. %), chlorohexidine, Nipa-Ester® or antibiotics.

The liposomes of the invention are obtained from the mixture of the bilayer-forming lipids with at least a portion of unsaturated fatty-acid chains and an aqueous solution of bile acid and/or at least one of the derivatives thereof by supplying mechanical energy. This can, for instance, by done by stirring, shaking, homogenizing or by other actions of shear forces, for instance by filtering. In a preferred embodiment, the heterogenous mixture of lipid and bile acid or bile acid derivative is filtered once at a small excess pressure, preferably $10^5$ Pa to $6 \times 10^5$ Pa, with a filter having a pore size of 0.1 to 0.8 μm, preferably 0.15 to 0.3 μm, and especially preferably 0.15 to 0.22 μm. The upper limit of the pore diameter is expediently 0.22 μm for sterile liposome preparations. Mechanical energy may selectively be supplied, for instance with the aid of a stirring mechanism. Storing of the heterogeneous mixture without any interference with the system by the supply of mechanical energy leads to an auto-formation of liposomes after several months.

The liposomes of the invention are suited for use as drugs. They may here be applied in any manner that is customary in the medical field, e.g., dermally, intravenously, orally, subcutaneously, intramuscularly or intraperitoneally. The liposome preparation produced according to the invention is diluted in the ratio of 1:1 to 1:1000, preferably 1:1 to 1:20, with physiologically tolerated diluents. An effect can be observed within a short period of time and is expressed in the case of a therapy by a rapid decline in the clinical symptoms, as will be shown below.

Furthermore, a method for preparing liposomes is provided according to the invention, wherein the bilayer-forming lipids which contain, at least in part, unsaturated fatty-acid chains are mixed with an aqueous solution of bile acid and/or at least one of the derivatives thereof, wherein before mixing, the lipids are present either as such or are dissolved in a water-miscible solvent, and mechanical energy is subsequently supplied to the mixture.

The mechanical energy may be supplied by shaking, stirring, homogenizing or non-recurring filtering. The filtration is preferably performed at a small excess pressure, in particular, $10^5$ Pa to $6 \times 10^5$ Pa; the pore size of the filter is 0.1 to 0.8 $\mu$m, preferably 0.15 to 0.3 $\mu$m, and especially preferably 0.15 to 0.22 $\mu$m.

The mixture of the bilayer-forming lipids and the aqueous solution of bile acid and/or one of the derivatives thereof is prepared at 0° C. to 95° C., preferably at 18° C. to 70° C., and especially preferably at 18° C. to 38° C.

A pH of 4.0 to 10.0, preferably 5.5 to 7.5, should be observed when the mixture is prepared.

The liposomes prepared according to the invention by means of filtration by a filter having a pore size of from 0.22 to 0.45 $\mu$m have a diameter of about 50 to about 200 nm, the mean diameter being about 80 to about 120 nm. The diameters were determined by means of electron microscopy and photocorrelation spectroscopy.

The liposomes according to the invention are preferably used for preparing drugs. Surprisingly enough, it has been found that the liposomes of the invention are effective against a group of very different diseases, such as allergies, viral infections, inflammations, and a specific kind of pain. All of these diseases, however, have in common that they originate from a specific "lability" or "acceptance" of the plasma membrane of the affected cells. For instance, specific allergic reactions are triggered by the destabilization of the mast cell membrane, nerve impulses are generated by destabilized cell membranes, and viruses can only penetrate into those cells whose cell membrane exhibits the necessary acceptance at the time of infection (details will be described in the following sections I to V).

The liposomes of the invention have antiviral (virustatic), antiallergic, antiphlogistic, analgetic and regenerative or tissue-protecting properties. A basic effect is the influencing of the cell membrane by the liposomes after interaction (fusion) with cells; mediator release (exocytosis) is perhaps suppressed thereby on the one hand, and the fusogenity of the cells with virus particles is perhaps reduced on the other hand. Antioxidant-containing liposomes, in particular, are probably responsible for the neutralization of highly reactive oxygen radicals in the extracellular and intracellular space. With nociceptors, there might be an increase in the stimulus threshold or decrease in the action potential after fusion and/or an influencing of receptors (for instance of the opioid receptors) or, accordingly, of associated membrane proteins. In case the liposomes of the invention exert an effect on membrane proteins which influence the intracellular amount of "second messengers", such as cAMP, specific peptide- or proteohormone-correlated diseases (such as diabetes) or growth factor-dependent cell disorders (for instance tumor formation and growth) could also be treated.

The liposomes of the invention are capable of penetrating into the body tissue, for instance into the skin. They interact there, probably through fusion, with cells and modify the plasma membrane not so much chemically but physically, since the liposome membrane consists of components which are also found in the plasma membrane. Details thereof follow from the experiments described under "Antiviral Treatment" (subsequent section I), according to which a preincubation of the target cells (vero) with the liposomes reduces the acceptance of said cells for a subsequent herpes virus infection considerably (to less than one third). After liposomes have fused with cells, it might also be that the cells are less capable of performing an exocytosis of vesicles and thus of releasing mediators. It is only after a certain time when the substances (lipids and bile acid and/or the derivatives thereof) introduced by the liposome fusion into the cell membrane are again released by physiological processes that the cell is enabled again to perform the original exocytosis and endocytosis.

These physical effects on the cell membrane may also provide for therapeutical approaches to pathologically changed body cells in which changes in the cell surface are also responsible for the pathological event.

For instance, the ability of tumor cells to perform active locomotion, homo- and heterotypical aggregation and the various recognition and adhesion mechanisms are indicative of a cell membrane deviating from the normal state.

As a rule, it can be assumed that physiological liposomes, optionally including the above-mentioned additives, can be used for treating all those symptoms where (as described above) a certain "lability" or "acceptance" of the cell membrane is found to constitute at least one of the principles causing the disease. Since this is not always obvious, five symptom complexes shall be explained (see below, sections I–V). Moreover, specific additional therapeutical mechanisms of the liposomes, which will be discussed in more detail in the respective sections, exist for individual diseases.

The liposomes of the invention are especially used for the prophylactic and/or therapeutic treatment of diseases caused by viruses with lipid envelope, in particular viruses from the group consisting of the families Herpesviridae, Orthomyxoviridae, Retroviridae and Hepadnaviridae.

Another preferred use is the one for the prophylactic and/or therapeutic treatment of diseases caused by viruses without lipid envelope, in particular viruses from the group consisting of the families Adenoviridae, Papovaviridae and Picornaviridae.

The liposomes of the invention are further suited for treating diseases caused by mycoplasmataceae, chlamydiaceae and rickettsiaceae.

A principal field of use of the liposomes according to the invention is the prophylactic and/or therapeutic treatment of allergic diseases, in particular of the skin and mucous membrane. The liposomes according to the invention are suited for use in the preparation of medicaments for the prophylactic and/or therapeutic treatment of contact, food and drug allergies. Other possible uses consist in the preparation of drugs for the prophylactic and/or therapeutic treatment of allergies of the atopic type, in particular neurodermatitis. When used in the preparation of a drug for treating neurodermatitis, the medicament may have added a local anaesthetic in the concentrations allowed for skin protectives. Preferred local anaesthetics are lidocaine or tetracaine.

Furthermore, the excellent properties of the liposomes according to the invention permit the use thereof in the preparation of a skin protective suited for use in commercial skin protection. Another possibility of use is the employment for the preparation of an agent for the prophylactic and/or therapeutic treatment of dry skin, such an agent having urea optionally added thereto.

A field which is entirely independent of the above-mentioned possible uses is the employment of the liposomes of the invention for preparing a drug for the prophylactic and/or therapeutic treatment of pain. It has been found that the inventive use is, in particular, suited for the prophylactic and/or therapeutic treatment of tonic pain and for the prophylactic and/or therapeutic treatment of painful muscular tensions, postoperative scars or phantom-limb pain.

Another preferred embodiment is the use of the liposomes of the invention for preparing a drug for treating non-articular rheumatism.

Furthermore, it has been found that a drug containing the liposomes according to the invention is well suited for treating dental neck sensitivity. Another possible use is the use of the inventive liposomes for the prophylactic and/or therapeutic treatment of allergically and/or virally caused eye inflammations. Furthermore, the liposomes of the invention can be used on the eye for the prophylactic and/or therapeutic treatment of the dry-eye symptom.

Furthermore, the liposomes of the invention are quite generally suited for the preparation of a drug for the prophylactic and/or therapeutic treatment of inflammatory diseases.

According to another embodiment of the present invention, the liposomes of the invention are used for preparing drugs for the prophylactic and/or therapeutic treatment of damage caused by natural or synthetic ultraviolet light, by radiation from radioactive decay, by X-rays or heat.

Furthermore, it has been found that the liposomes of the invention are suited for treating rheumatoid arthritis.

In accordance with the invention the liposomes can also be used for preparing drugs for the prophylactic and/or therapeutic treatment of geriatric complaints and as radical scavengers and/or as immediate aid in different states of shocks.

As explained above in detail, the liposomes of the invention influence the membrane potential of cells fused therewith. Therefore, the liposomes of the invention are extremely well suited for the treatment of diseases which are fully or partly caused by membrane potentials of the corresponding cells, which potentials differ from the normal state.

As a result of the fusion of the inventive liposomes, it is not only the membrane components thereof, but also the aqueous compartment that is introduced into the cell. The liposomes are therefore also suited for preparing drugs for the prophylactic or therapeutic treatment of diseases which are entirely or partly caused by a fluid loss of the affected cells which differs from the normal state.

It has already been pointed out that the surface tension of cells which fuse with the liposomes of the invention is changed. Therefore, the liposomes of the invention are also suited for preparing drugs which serve the prophylactic and/or therapeutic treatment of diseases which are fully or partly caused by a surface tension of the corresponding cell membranes that is increased in comparison with the normal state.

Another possible use of the inventive liposomes lies in the preparation of drugs for the prophylactic and/or therapeutic treatment of diseases caused by damage due to oxidative processes on cellular and/or extracellular structures.

As has already been mentioned above repeatedly, the membrane properties which have been changed due to fusion with the liposomes of the invention may influence the concentration of the cellular "second messengers". The liposomes of the invention are therefore suited for the prophylactic and/or therapeutic treatment of diseases caused fully or partly by an intracellular concentration of one or several "second messengers" which deviates from the normal state.

Finally a drug is claimed which contains the liposomes of the invention:

Various possibilities of using the inventive liposomes shall now be described in the following sections I to V. In cases where hypotheses can be advanced why the liposomes of the invention have such diverse and unexpected effects, possible explanations will be discussed.

I. Use of the physiological liposomes of the invention for the prophylactic and therapeutic treatment of viral infections The present invention relates to the prophylactic and therapeutic use of the liposomes of the invention for the treatment of viral infections in vivo and in vitro. The liposomes of the invention act on entirely different types of viruses. No negative influences of the liposomes on the cells or organisms could be detected in the tested effective concentrations.

The principles of action of all of the former antiviral agents (except for active and passive immunization and support of the immune defense by endogenous substances, such as interleukins and interferons as well as amantadine and rimantadine whose mechanism of action is not precisely known yet) are based on an inhibition of virus-specific enzymes (polymerases), for instance, on the inhibition of the viral DNA or RNA synthesis by nucleoside analogues (9). Since viral enzymes are similar in kind and action to endogenous enzymes, all enzyme inhibitors are also toxic for cells and for the host organism, respectively, from a certain dosage onwards. This applies also to the treatment with nucleoside analogues. It is not only the fast replication of the DNA or RNA strands of the viruses which is here inhibited, but also that of endogenous hereditary-material molecules which replicate during therapeutic treatment. With a systemic application, the first damage is above all observed in the marrow, intestinal epithelium and in the hair cells. The long-term damage which is to be expected in the form of mutagenic changes must be viewed especially critically. A treatment must therefore be regarded as a tightrope walk between an antiviral effect which should be as effective as possible and an intoxication of the affected person which should be as low as possible. Up to the present invention there has, in the long run, not been any antiviral substance that has been without any major toxic side effects for the affected person. In contrast to an antibiotic treatment of bacterial infections, viral infections in man and animal are virtually exclusively fought by the endogenous immune system whose failure in case of an immunodeficiency points to the helplessness of modern therapies (e.g. AIDS).

Surprisingly enough, it has been found that physiological liposomes according to the invention (i.e., liposomes without any real antiviral therapeutic) are able to prevent the propagation of viruses. The effect is possibly due to a competitive inhibition of the binding of viruses to the membrane by physiological liposomes. The increased affinity of the viruses to their hosts cells, which is possibly caused by receptors, can be compensated for in the "liposome treatment" by the far higher number of liposomal reaction partners. The highest liposome concentration tested in the present invention is, on average, $4.4 \times 10^{14}$ liposomes per ml. By comparison, $10^8$ viruses or PFU (plaque forming units) per ml is the highest herpes-simplex concentration in vitro. It is unknown which virus concentrations are present in vivo, for instance in a virus-caused tissue lesion. It is however assumed that considerably less infectious herpes viruses are found per ml of tissue fluid. The affinity of the viruses to the host cell would therefore have to be greater, by many powers of ten, than the affinity to the simultaneously offered liposomes if the viruses were only "hindered", but not destroyed by the liposomes (the last-mentioned case might perhaps apply to part of the virus population; see following results). The subsequently described results show that the enormously high number of applicable liposomes actually creates a virustatic effect, which is possibly due to "mechanical" inhibition.

A preliminary explanation for the strong antiviral properties of physiological liposomes as observed might be, for instance, that liposomes of the employed type penetrate into organs, tissues and body fluids, fuse there with viruses or cells and/or "occupy" intercellular "free spaces". The effects developed by them are presumably multiform and could be due to one or several of the following causes, possibly with different importance, depending on the type of tissue or cell and the respective virus:

1. the plasma membrane of animal cells can only fuse with a limited amount of particles or vesicles within a specific period of time (depending on the type of cell). The binding preceding the endocytosis of viruses takes place via so-called "coated pits", plasma membrane hollows coated with specific proteins, which amount to about two percent of the surface of a typical animal cell. It might be that the surfactants introduced by cell-membrane/liposome fusion "disturb" the spatial structure of those cell-membrane components which form the "coated pits", thereby preventing the accumulation of viruses at least for some time. When a cell has already absorbed a sufficient number of liposomes, it is "inert" to the penetration of viruses for some time.

2. The incorporation of liposomal components (e.g. phospholipid and/or cholate) into the plasma membrane could lead to slight changes in the membrane (e.g. membrane potential, see section III) which render more difficult a viral exocytosis or also destablize the exocytated viral envelope structure.

3. The diameters of the used liposomes are within the size range of most viruses, namely between 20 and 300 nm. As a consequence, liposomes resemble many viruses, partly also in their physicochemical surface characteristics. Liposomes could also be designated as a kind of "pseudovirus" in the sense that they have a similar mode of propagation as used by many genuine viruses due to their size and physicochemical properties. Liposomes which easily penetrate in great numbers, for instance into the skin tissue, fake the presence of viruses in said tissue, possibly impede also viral binding sites, thereby preventing genuine viruses from propagating any further. The antiviral effect caused by such liposomal "pseudoviruses" would consequently be manifested by a simple mechanical inhibition or suppression reaction.

4. Because of the interaction of liposomes, in particular, with bivalent ions, these change the physical conditions in the intercellular space. This might result in a shift in the ion equilibrium in such a manner that viruses are impeded in their propagation. This could especially be true for the increased calcium values required by some viruses.

5. Furthermore, an increased antiviral effect follows from the addition of reducing substances, such as ascorbic acid and/or sulfite, as individual substances or in a mixed state. It might be that the liposomal introduction of such substances into the tissue has the effect that oxidizing noxae (radicals from lysed cells) which are released through viral propagation are intercepted in time, and healthy neighboring cells are thus less damaged. It might also be that liposomes whose components are kept in reduced form through corresponding additions have generally better physiological properties.

6. Some virus families, such as Herpesviridae and Rhinoviridae, are characterized by lability towards pH values ranging between 5 and 6. The increased antiviral effect of ascorbic acid-containing or other "acid" liposomes could be explained thereby.

7. Liposomes can interact with viruses, possibly fuse with viruses and finally neutralize them. To this end, and in accordance with the results of Example 1, a certain number of liposomes are needed for forcing viruses to perform such an interaction. The effective density follows mainly from the size of the viruses and the liposomes. The neutralization itself could be performed, in the case of enveloped viruses, simply by exceeding a limit size of importance to the respective virus (each virus has a specific maximum size) and, in the case of naked viruses, by enveloping the same with the liposome membrane. It is however likely that the viruses are destabilized by the surfactants transmitted after fusion with the liposomes.

8. Liposomes introduce membrane material (lecithin) which can be exploited in tissue lesions caused by viruses, and this could accelerate the regeneration of destroyed areas.

Former tests with test persons reveal a definitely antiviral effect of the liposomes of the invention against representatives of the alpha herpes viruses, such as herpes simplex and varicella zoster, and beta herpes viruses such as cytomegalovirus. The viral efflorences in herpex simplex considerably decline within one day. The pains which can be observed with some patients during an acute phase of the infection are greatly reduced by the liposomes or will disappear entirely. In one case liposomes turned out to be effective against an aciclovir-resistant herpex simple infection (treating test study at the Ramble Hospital, Barcelona). In animal tests a therapeutic effect could be achieved in the treatment of the infectious bovine rhinoracheitis, a disease caused by the bovine herpes virus (type 1) in cattle.

In-vitro tests with herpes simplex type 1 (HS 1/5886) with monkey kidney cells (vero cells) reveal, in dependence upon the respective conditions, a more than 99% reduction of the PFU (plaque forming units) after a single application of physiological liposomes. It becomes apparent from the results of different test approaches that liposomes interact with viruses and make them harmless; their action is additionally intensified by membrane changes of the host cells. Hence, or at least in this test system, the antiviral effect of physiological liposomes might predominantly be based on effects as described above under 1. and 7. as a possible explanation. This conclusion does not automatically apply to an employment in vivo, i.e. to the tissue or the whole organism. In-vitro tests with HIV-1 (Retroviridae) and influenza viruses (Orthomycoviridae) also reveal a definite virus reduction after administration of liposomes.

Should the antiviral properties of physiological liposomes at least partly be based on their similarity with the envelope structures of, for instance, the alpha herpes viruses and Retroviridae, one could prognosticate that the representatives of the following vertebrata-infected virus families can be treated with physiological liposomes:

Herpesviridae (alpha-, beta-, gamma-herpes viruses)
Togaviridae (e.g. rubella virus)
Poxviridae (e.g. small pox virus)
Paramyxoviridae (e.g. mumps, measles virus)
Orthomyxoviridae (e.g. influenza viruses)
Coronaviridae (e.g. IVB)
Bunyaviridae (e.g. hantaan virus)
Areanviridae (e.g. lassa virus)
Retroviridae (e.g. HTLV-1, HTLV-2, HIV-1, HIV-2)
Flaviviridae (e.g. yellow-fever virus)
Rhabdoviridae (e.g. rabies virus)
Hepadnaviridae (e.g. hepatitis B-virus)
Toroviridae (e.g. Berne virus)
Filoviridae (e.g. Marburg virus)

It could be shown in a test against warts presumably induced by papilloma viruses (*Verrucae planae* juveniles) that these disappeared after daily repeated application of physiological liposomes within three weeks. This result, as well as successes with rhinovirus infections (Picornaviridae) reveal, however, also so-called naked viruses as possible therapeutic objectives:

Adenoviridae
Caliciviridae
Papovaviridae
Parvoviridae
Picornaviridae
Reoviridae
Iridoviridae
Birnaviridae Other intracellular parasites which infect their host cells through a similar mechanism as do viruses could perhaps be fought as well. Such microorganisms include, in particular, the representatives of rickettsiaceae, bartonellaceae, chlamydiaceae and mycoplasmataceae. With a systemic application of liposomes, some of the virus-induced autoimmune diseases and tumor diseases that have so far been considered to be incurable could also be treated.

The unspecific antiviral effect of physiological liposomes points to the model of action listed under Example 1 and thus to a broad use of this remedy against many different viruses in plants, animals and human beings.

Physiological liposomes are also suited as antiviral addition in specific bacterial or fungal cultures and in vegetable or animal cell and tissue cultures.

Long-term tests with voluntaries furnish evidence that the use of physiological liposomes as a prophylactic, for instance against herpes simplex type 1, proves to be extremely efficient. In case one or several of the above-mentioned antiviral modes of action of physiological liposomes are applicable, resistances thereto, as are virtually found to all common antimicrobial therapeutics in the course of time, are very unlikely to be developed by the viruses.

II. Use of the physiological liposomes of the invention for the prophylactic and therapeutic treatment of allergic reactions The liposomes of the invention are further suited for the local and systemic inhibition of allergic reactions of man and animal.

As is generally known, allergic diseases increase, at least in industrial countries, from year to year, with the causes being not fully elucidated. Apart from mucosal allergies, such as "hay fever", skin allergies are very frequently found, caused by contact, e.g., with yeast fungi, bacteria, insects, house dust, pollens, chemical substances or medicinal agents, as well as adjuvants in cosmetic and pharmaceutical formulations and many other things. A frequent cause for locally defined contact allergies is the wearing of jewelry. The majority of persons wishing to wear jewelry are prevented from doing so by allergic reactions. Pieces of relatively easily oxidizable metals (all except for high-karat gold and platinum alloys) fall, in particular, under the category of "incompatible" jewelry. Incompatibility, or in other words the allergy, starts in extreme cases already a few minutes after the jewelry has been put on, and is expressd by itchiness of the corresponding skin part up to unbearable pain. Depending on the degree of allergy, persons affected thereby have often only the choice to either dispense with the wearing of jewelry altogether or to use high-karat gold or platinum jewelry.

An allergic skin reaction which is also widespread can be observed after radiation with ultraviolet light of a specific wavelength. The persons affected react on the skin parts exposed to the radiation (sun, ultraviolet tanning) with erythema, urtication, and pain. Food allergies are also widespread, e.g. against gluten. Allergic reactions of an atopic kind which are caused by a multitude of internal and external factors have been observed very frequently in the past few years. This includes above all neurodermatitis. The endotoxic shock produced by mediator release belongs to the allergic diseases of the atopic type which are still difficult to treat.

Internal and external means are available for treating such allergies. As a rule, skin allergies are treated with the aid of external means; in serious cases internal means are additionally administered. Since the cause of a resulting skin allergy is often not known, a reliable diagnosis is made very difficult. As a consequence, so-called "harmless" antiallergics are used for treatment at the initial stage, which agents often just alleviate the complaints or do not show an effect at all. A physician is therefore forced to continue his/her treatment and to resort to dermatics, antibiotics and antimycotics (with secondary infections allergy-damaged skin parts), i.e., to drugs which contain chloramphenicol, rifampicin, flumethasone, dexamethasone, triamincinolonacetonide or hydrocortisone, just to mention a few. Many of these "hard" drugs have limited uses and may, in turn, cause side effects, such as skin atrophy, steroid acne, etc. Dermatologists fear, e.g., the rebound effect after the administration of cortisone has been discontinued. Furthermore, they often dry the skin and must not be brought into contact with the eye conjunctiva (see section IV). A problem which is found in the administration of external antiallergics is insufficient absorption through the skin. Penetration of the drugs is rendered especially difficult if these are water-soluble. A comparable problem arises when the active substance is lipophil and must be applied in the form of a crystalline suspension. The effectivity of external antiallergics is therefore considered to be unsatisfactory.

Similar problems arise in the control of hay fever. To be able to treat these allergic reactions of the nasal mucous membrane after contact with corresponding allergens, such as pollens, house dust, substances of animal hair, etc., the use of "hard" pharmaceuticals which are often applied in the form of an aerosol (e.g. hydrocortisone) is also required. However, a prophylactic use of such therapeutics is advised against because of the numerous side effects. A genuine prophylactic without any side effect has so far not existed.

Already existing studies show (1, 2, 3) that liposomes can deeply penetrate into the dermis of the skin within a short period of time (in some cases within a few minutes). Liposomes penetrate into mucous membranes within seconds. Hence, a penetrating effect of locally applied liposome suspensions can be assumed.

The inhibitory effect of physiological liposomes of the invention (without addition of an active substance) on local allergic reactions has not been clarified in detail, but is presumably due to one or more of the following explanatory models:

1. Liposomes prepared from lipids or lipoids, for instance from phosphatidyl cholines, penetrate into the mucous membrane or the dermis of the skin, fill the intercellular spaces and prompt the cells existing there to "swell" by fusion with the liposomes. As a result, the tissue becomes perhaps "denser", thereby preventing the penetration of allergens and the propagation of mediators. It might also become more resistant to mechanical load thereby.

2. Liposomes which have penetrated into the skin or mucous membrane and therefore exist also in the intercellular spaces absorb released mediators (e.g. vasoactive amines), thereby inhibiting the propagation thereof up to the vascular endothelium cells. This prevents, for instance, a vasodilation with increased vascular permeability. The calcium ions involved in numerous membrane processes are also absorbed by liposomes and only released again gradually.

3. Liposomes presumably interact by adsorption, fusion and/or endocytosis also with the basophilic granulocytes and mast cells and possibly change the membranes thereof (plasma membrane or also intracellular membrane system), so that the release of mediators is impeded.

4. The liposomes penetrating into the lower skin or mucous-membrane layers displace harmful substances located in the intercellular spaces into the lymphatic and vascular system and/or absorb them, thereby accelerating the metabolism thereof (possibly through phagocytosis by means of cells found in the skin, such as macrophages).

5. As for the special case dealing with allergies to specific metals, the metal ion-absorbing properties of liposomes can be used as an explanation for the antiallegic effects observed: In case of skin contact atoms or ions are separated in minimum amounts from metals by way of chemophysical processes. These bind most of the time to endogenous molecules and often act in these compounds as allergens (hapten-carrier complex) which trigger the corresponding rejection reactions. In case liposomes are positioned at those skin points getting into contact with the allergen, these will absorb the released metal ions (own investigations), possibly before the same are able to bind to a carrier. The liposomes themselves are gradually absorbed by body cells and metabolized. The metal ions are complexed by way of numerous intracellular detoxification mechanisms (for instance metallothioneine) and discharged.

6. It might also be that some of the basic substances of the liposomes (essential fatty acids such as linoleic acid), or their products of metabolism, are active as antiallergenic substances.

7. Tests with several test persons have shown that especially bile acids as surfactants give very effective antiallergic liposomes. This could be explained by the possible effect of bile acids on the intracellular cAMP level and/or the release of prostaglandins and on physical changes in the plasma membrane with a view to a changed membrane potential. The effect of histamine on the target cells thereof is due to binding to special receptors ($H_1$, $H_2$, $H_3$) which, in turn, activate corresponding enzymes via associated G proteins (5). The resultant second messengers (cAM, $IP_3$, DAG, $Ca^{2+}$) activate numerous intracellular enzymes. Bile acid or bile acid derivatives or the changes triggered by them in the cells could influence one or more of the membrane-based molecules of this transmission path or disturb the interaction thereof.

8. The antioxidative properties, in particular, of vitamin C-containing liposomes permit the interception of radicals and non-radical noxae in the intercellular and extracellular space.

The results which have so far been obtained point to main factors for the effectiveness of physiological liposomes, as were described under 1, 3, 7 and 8.

The present tests show an allergy-inhibiting effect of the physiological liposomes of the invention. The liposomes described here consist exclusively of substances having a biological origin, such as phosphatidyl choline (lecithin), of which the majority of the cell membranes at least of all higher organisms consist. The excellent antiallergic effects of these liposomes permit, for the first time, a harmless, prophylactic application in the form of a cosmetic or natural remedy and/or prophylactic or therapeutic application as a drug.

The invention provides for a means for the local application of liposomes to act against skin or mucous-membrane allergies and for the systemic application against allergies of the digestive tract and generalized allergies (for instance allergic states of shock). The physiological liposomes can be combined, for instance, with ascorbic acid and other antioxidants or reducing agents according to requirements.

The liposomes are directly used as a liposomal suspension according to the invention, preferably in purely liquid form, optionally as drops, aerosol or infusions, as addition to medicinal baths or also by means of transdermal therapeutic systems, such as plasters, optionally also under addition of gel-forming agents or other thickening means or mono- or polyvalent alcohols.

Physiological liposomes are excellently suited for controlling skin or mucous membrane allergies. The term mucous membrane allergy predominantly covers allergic reactions of the nasal, buccal or ophthalmic mucous membrane which are triggered by contact with corresponding allergens. The immunological mechanisms which take place here are similar to those of the skin allergies discussed hereinafter with reference to the earring allergy. The term skin allergy covers syndromes of different geneses of which all, however, lead to a similar, more or less locally defined skin reaction (allergy).

Incompatibility with earrings as can very often be observed is to serve as an example of such a locally occurring allergic reaction. Two, possibly causally unrelated allergic reactions can here be observed: On the one hand, an allergy specifically directed against specific substances (allergens), such as nickel, in the case of which patients can often just wear high-karat gold or platinum jewelry without symptoms; on the other hand, a kind of mechanical urticaria (urticaria caused by pressure) in the case of which it is solely the mechanical load on the earlobe that leads to allergic reactions. The stronger the mechanical load created by ear pins or clips, the more vehement is the reaction, with small hoops being best accepted due to a low weight and small cross-section of the ear-penetrating part. Of course, both types of allergic reactions can be found with different weight in one and the same patient. As for the first case, a classical form of allergic reaction which has been known since a long time can be indicated as the mechanism, in which antigen-specific IgE antibodies are seated on the surface of immunoreactive seals existing in the skin, for instance, mast cells and basophilic granulocytes. In case of antigen contact with the cell-bound IgE antibodies a signal is transmitted into the cytoplasms of these cells, which results in the long run in a release (degranulation) of mediators from the storage vesicles, such as histamine. The vasodilatation caused thereby in the corresponding area leads to swelling, reddening and heating of the earlobe. Since the degranulation of basophils and mast cells reaches its optimum at 37° C.–38° C., this process becomes increasingly stronger due to the increasing ear temperature (see section V). The amount of tissue fluid increases due to the increased vascular permeability in parallel therewith, and this will further increase the pressure prevailing in the earlobe. The nerve cells of the earlobe register these changes with a corresponding pain sensation. The passage of blood plasma components into the tissue can be so pronounced that, with some patients (also without earhole), blood plasma exits massively through the skin pores of the earlobe. The symptoms will fade only slowly, the ear remaining pressure-sensitive, sometimes over weeks. In extreme cases necrotic processes can be observed that result in permanent changes in the earlobe. No special antigen takes part in the mechanical urticaria for causing the same symptoms in the long run, as just described. It can be assumed that a massive appearance of skin-bound basophils and mast cells and/or of basophils and mast cells which are relatively instable in their degranulation release their mediators solely by mechanical action (pressure), thereby causing the above-mentioned reactions. Since hormonal physiological antagonists, such as catecholamines, suppress the release of mediators under normal conditions, the time variations in the sensitivity of individual patients can also be explained thereby. Therefore, more pronounced allergic reactions can be observed under stress conditions when the natural hormonal control of the physiological antagonists is disturbed.

All fields in which an allergy, such as urticaria, eczematic dermatitis or mucous membrane allergy, is to be expected (prophylaxis) due to an imminent body contact of a patient are regarded as fields of applications of the present invention; for instance:

in the medical field upon use of: plasters, dressing means, topic drugs, electrodes, sensors, short-wave electromagnetic radiation, wound closures (clamps), infusion catheters, prostheses and possibly also skin transplantations, for instance, with skin substitutes;

in dentristy upon use of makeshifts, dental prostheses;

in "everyday life" upon contact with: specific foodstuffs, plant pollens, substances of animal hairs or skins, house dust, jewelry, glasses, watches, hearing aids, clothing, detergents, cosmetics, ultraviolet light, etc.;

as commercial skin protection.

Diseases accompanied by allergic etology, such as the atopic eczema/neurodermatitis, are regarded as other therapeutical fields. Furthemore, systemic treatments of generalized allergic reactions, such as allergic shocks, are regarded as further fields of application.

First tests with voluntary test persons have shown that a non-recurring application of physiological liposomes suppressed, in so far all cases, the allergic reaction to earrings for several hours to several days. The testing of physiological liposomes in the form of aerosols shows an extreme improvement of the allergic state in part of the test persons with hay fever; the liposomal application often led to a complete inhibition of the allergy (see Example 2). Similar positive results were obtained in tests regarding sun allergy, contact allergies (inter alia, to arm, finger or neck jewelry, watches), allergically caused eczemae, such as Erythema exsudativum multiformis, and neurodermatitis. A patient with a severe endogeneous eczema in the case of which a corticoid treatment was without success because of the immediately recurring rebound effect has been symptom-free for one year after treatment with physiological liposomes. Ascorbic acid-containing liposomes have turned out to be often especially effective in these kinds of tests, which points to the participation of oxygen radicals released as mediators.

III. Use of physiological liposomes of the invention for the prophylactic and therapeutic treatment of pain and muscular tensions The liposomes according to the invention can further be used for treating tonic pain and the consecutive symptoms related therewith. No negative effects of the liposomes could be detected in the effective concentrations tested. The nociceptors which are primarily generating pain, the morphologically least differentiated receptors, are mainly of importance to the treatment with physiological liposomes of the invention. These non-myelinated nerve endings are the sense organs for pain in almost all tissue. They extend, for instance, in the epidermis up to the stratum lucidum, i.e., shortly below the cornea layer. Two fiber systems (Aδ and C fibers) having different rates of conduction conduct the pain impulses to the central nervous system. The presence of a rapidly conducting system and a slowly conducting system explains the two types of pain observed: The first pain stimulus causes a "bright", piercing, well-localizable sensation which is followed by a "dull", boring, hardly localizable pain. Starting causes for the so-called nociceptor pain are tissue lesions caused by pathological changes in the interior. This leads to a change (e.g. increase in cell membrane instability) in or destruction of cells, whereby algogenic substances are released. The formation of prostaglandin $E_2$ which sensibilizes the nociceptors for the algogenic substances is very important in this acute process. Algogenic substances, such as histamine, calium, kinins, serotonine, and substance P, are either released via ion channels (for instance calium) or exocyted (for instance histamine). The initial steps in the pain generation and allergy generation are here similar. With some substances such as histamine, prostaglandins and kinins, one can talk about an almost identical initiation process (see section II). This might also furnish the main explanation for an effect of physiological liposomes on both types of diseases.

So far there have been no analgesics that do not have undesired side effects. Possible respiratory paralysis and the danger of habit formation in opioid-containing analgesics, as well as damage to the gastro-intestinal mucous membrane in the case of salicylic acid derivatives could here be mentioned as examples. Because of the complexity of the processes involved in pain generation and processing, there are many, entirely different approaches to produce analgesia (only the most common mechanisms are here listed; (5));

corticosteroids inhibit the formation of arachidonic acid and thus the metabolism thereof into prostaglandin $E_2$;

non-steroid antiphlogistics inhibit the formation of cyclic endoperoxides and in this respect also the formation of prostaglandins;

opioid analgesics suppress pain sensation by assaulting the central switching points of the nociceptive system;

antiphlogistic analgesics act, on the one hand, directly in the area of the nociceptors in the damaged tissue, but on the other hand also centrally, presumably also by inhibiting the prostaglandin synthesis;

antipyretic analgesics are probably effective in a similar way as antiphlogistic analgesics through inhibition of the prostaglandin synthesis.

All of the substances used therefor generate undesired, more or less strong side effects (as mentioned above) because they interfere with physiologically important processes.

The analgesic effect of physiological liposomes can be detected by testing test persons having different symptoms, with Vitamin C-containing liposomes turning out to be sometimes more effective (possible modulation of the prostaglandin metabolism by vitamin C or other effects (see 11)).

As already described in sections I and II, the pain caused by viral infection or allergy disappears immediately in most cases after a liposome application. At least part of the mediators which are released by virally caused tissue lesions or allergic reactions are algogenic substances which alarm the nociceptors of the corresponding tissue. An objective assessment which furnishes proof of an action of physiological liposomes on nerve activity follows from the finding determined in Example 3 on the isolated intestine of a guinea pig. The pronounced inhibiton of nerve activity in the case of relatively low liposome concentrations furnishes proof of the surprising efficacy of the cholate liposomes. The cholate-free liposomes used as a control lead to a stimulation of the nerves. Since an influence of the liposomes on the ion composition of the fluid is negligibly small due to the relatively small amounts of liposomes in the organ bath, but since cholate-free liposomes effect such a pronounced stimulation, it must be assumed that these liposomes, too, directly interact with the tissue or the cells. It is known from numerous experiments that surfactant-containing liposomes have a greater loss of enclosed hydrophilic small ions or molecules than surfactant-free liposomes. The cholate liposomes which are here used also have this property; i.e. surfactant-containing phospholipid membranes have a slightly increased permeability (in both directions) for such substances. When liposomes having a relatively great cholate amount (as the ones used here) fuse with cells, the entrained surfactants transmit the slightly increased membrane permeability, for instance for ions such as $Na^+$ and $K^+$, to the cell membranes. The membrane potential (resting potential) is shifted on account of the now increased ion flow towards the "firing level" (10). Although this increases the excitability of the cell, the decrease in action potential corresponding to the depolarization simultaneously decreases the transmitter substances to be released (less vesicles are released), thereby effecting a reduced excitation of the postsynaptic cell (4). This presynaptic efficiency could be confirmed in further experiments with acetyl choline- or histamine-stimulated isolated guinea pig intestine. By contrast, a change in the membrane potential away from the "firing level" follows for a fusion of surfactant-free liposomes with cells, which consequently entails an increased action potential and an increased release (increased vesicle release) of transmitter substance. This leads to the observed stimulation of the intestinal contraction.

In contrast to the above-described therapeutical approaches to reduce pain, the model which is here presented starts from the assumption that the mediator release has an inhibiting effect and also that the membranes of the nociceptors are "stabilized" by fusion with physiological liposomes and/or that their resting potential is shifted towards "firing level". Moreover, an interaction with pain-alleviating receptors, such as the opioid receptors, can explain the analgesic effects of physiological liposomes. The question whether the receptors themselves, the mebrane-bound G proteins belonging to said receptors, or the adenylatecyclase (5) which takes also part in the signal translation, are influenced by liposome components or the physical changes following the fusions, or however whether the spatial arrangements of said structures in the cell membrane are changed relative to one another, calls for further investigation. An influencing of one or several of said factors would lead to a lowered cAMP level which, in turn, would entail numerous cell-physiological consequences (5)). It might however be that both mechanisms of action are operative at the same time. An analgesic effect of physiological liposomes can also be observed with pain in the case of which there is no visible impairment of the tissue. For instance, pain which occurs continuously or in intervals or in the vicinity of former injuries (fractures, postoperative scars, etc.), or as so-called non-articular rheumatism (fibromyalgia), will disappear within the shortest time by applying liposomes once or several times (depending on the patient). This would mean that such pains are produced by the nociceptors existing in the epidermis. An explanation of this phenomenon might be the so-called convergence-projection theory according to which illness of the depth structures and intestines sometimes project pain onto areas of the body surface which belong to the same or neighboring segments as the affected organ. Likewise, pain in the case of alcoholic polyneuropathy and diabetic neuropathy is fought against, possibly more effectively under addition of small amounts of calcium ions and vitamins of the B complex.

The effect of physiological liposomes on muscular tensions and relieving postures as occur, for instance, in the case of so-called rigidity of the neck and some sciatic complaints, has turned out to be very serious (see Example 3). These symptoms are based on a tonic reflex activity caused by chronic damage. The frequent pull on ligaments, tendons and joints causes tissue damage which increases the nociceptive reflex activity on account of the release of algogenic substances. Thereupon, the body will try to relieve these predamaged areas by increased muscle activity (cramped relieving posture), thereby starting a vicious circle. It becomes apparent from the application of physiological liposomes in the case of a stiff neck that the shooting pain caused upon turning of the head to the side of the muscular tension will ease off after about one minute following a single application of 2 to 5 ml of vitamin C-containing liposomes to the back of the neck and shoulder area. The head can again be moved to the side without pain although the muscular tension (mostly in the area of the trapezius muscle) remains for the time being. This tension will however disappear most of the time within one day after repeated application. Such complaints could so far only be remedied by repeated intramuscular injection of an analgesic (such as lidocaine) and oral administration of muscle relaxants after several days. Symptoms disappeared within one week upon daily application of vitamin $B_{12}$-containing liposomes in a tested case with a so-called tennis arm, i.e., with complaints showing already inflammatory damage.

Another example is here the treatment of the so-called dental neck sensitivity which makes patients very sensitive, in particular, to cold, heat, sweetness and acidity. The reason therefor is often a more or less exposed dental neck which, being e.g. additionally enlarged by acid damage in the area of the incisors, isolates the nociceptors within the tooth only incompletely from the "outside world". Chemical noxae as well as temperature differences pass through the porous dentine in hardly attenuated form to the nociceptors, thereby producing pain. The first application of physiological liposomes (rinsing or spraying) often causes a short piercing pain which possibly points to a change in membrane potential of the nociceptors due to fusion with liposomes. Upon further application the pain will be reduced gradually and finally disappear for ever. This easing off is accompanied by an increasing insensitivity to cold, heat, sweetness, acid, etc. In the end it will be enough to apply the physiological liposomes once or twice a day for treating dental neck sensitivity. Physiological liposomes also exhibit a very rapid analgesic effect in the case of broken skin, such as lesions of the nail bed. Other examples of the analgesic properties of physiological liposomes are found under section V.

A treatment which is without side effects in contrast to conventional analgesics favors physiological liposomes for broad use especially against symptoms which can nowadays only be treated with "strong" drugs, for instance, non-articular rheumatism and muscular tensions.

IV. Use of physiological liposomes of the invention for the prophylactic and therapeutic treatment of eye diseases Furthermore, the liposomes of the invention can be used prophylactically and therapeutically with different eye diseases, such as allergically or virally caused inflammations, irritations due to lacking or physiologically unfavorably composed lacrimal fluid and damage caused by chemical or physical action.

Many inflammatory eye diseases are triggered by allergens or viruses and lead, enhanced by bacterial superinfections, to impairments which will often be permanent. How sensitive the eye tissues are becomes already apparent from the fact that many general disorders (such as a cold) lead to eye diseases (such as conjunctivitis). The problems arising from present treatments of allergic and viral diseases have already been described in sections I and II, but are even more pronounced with eye treatments. For instance, the corticosteroids which are often applied in the case of inflammatory processes must not be used in case of damage to the epithelium of the cornea, as this might otherwise lead to a rapid progressive ulceration and possible perforation with loss of eye. Some antiallergics lead to a reduction of the lacrimal fluid, thereby creating new problems. The virostatics presently approved on the eye (e.g. aciclovir) can only be applied in case of emergency due to their strong side effects. The irritations which can often be observed and are caused by lacking or physiologically unfavorably composed lacrimal fluid (dry-eye symptoms) can only be treated with tear substitutes at the moment. The cumbersome application thereof (eye drops several times a day) and their always poor effect have not yet achieved any genuine break-through when these symptoms are treated. Damage caused by chemical or physical action, such as acid burns or burns, continue to pose serious therapeutical problems. A genuine treatment which is conducive to the regeneration of conjunctivas and epitheliums is not available at the moment. Many people cannot wear contact lenses because their eyes will not accept such a foreign body. When suffering from one of the following symptoms, they will not be in a position to wear contact lenses as vision aids at any rate: keratoconjunctivitis sicca or Sjögren's syndrome, disorders of the mucin layer (Stevens-Johnson syndrome, acid burns, vitamin A-vitaminosis and ocular pemphigoid) and reduced cornea sensibility. Furthermore, reduced lacrimal fluid (for instance after oral administration of antidepressants, antihistamines, diuretics or spasmolytics), chronic eye inflammations (blepharitis, conjunctivitis, etc.), and stay in low air humidity (for instance flying personnel) often lead to problems with contact lenses. Most of these causes can nowadays not be eliminated therapeutically to such a degree that contact lenses could be worn without problems for a long period of time. The grey cataract leading to blindness without surgical intervention could at least partly be avoided by administering high doses of vitamin C (800 mg a day) if the results obtained by experts at the Tufts University at Boston are confirmed (6). According to these results the antioxidative effect of vitamin C is responsible for inhibiting the lens oxidation caused by old age. Vitamin C amounts which are so high are, however, not tolerated by many people when administered orally. It would therefore be desirable to provide physiologically acceptable antioxidative substances in the immediate vicinity of the eye lens. At the moment, however, such a therapeutic agent does not exist.

As already described in sections I and II, the physiological liposomes of the invention have antiviral and antiallergic properties that suggest their use as an ophthalmic agent. In addition to these therapeutical approaches, there are above all regeneration-supporting (see section I, point 8) and protective abilities of physiological liposomes. The front part of the eye, above all the cornea and the neighboring conjunctivae are coated by a permanent liquid film. Apart from nutrients, salts and antimicrobial substances, this lacrimal fluid also contains substances which prevent rapid evaporation (e.g. lipids and mucins). The composition of the lacrimal fluid wetting the cornea and conjunctivae follows from the secretion of various glands, with the lacrimal gland secreting the main part of the fluid. Alveolar sebaceous glands (Meibomian gland), aprocrine glands (Moll's glands), as well as small accessory tear glands (Krause's glands) are seated in the eyelid itself. The bradytropic cornea, specifically the front cornea epithelium (5–6 layers of non-cornified epitheliums), is nourished by the lacrimal fluid through diffusion. This explains the special sensitivity of the cornea to disorders of the lacrimal fluid. As proved in Example 4 with reference to a group of patients having dry-eye symptoms, physiological liposomes, when applied externally to the eyelid, can contribute to a normalization of the fluid layer wetting the cornea and conjunctivae in many cases. The liposomes presumably penetrate through the very thin, multilayered cornified pavement epithelium of the front side of the eyelid, thereby supplying the lid-bound glands with fluid, nutrients and secretable substances (lipids) which slow down the evaporation of the eye fluid. Furthermore, studies with test persons having conjunctivitis caused by allergen or virus and with ceratitis show that upon application of physiological liposomes on the eyelid the "sand grain sensation" will disappear within a few minutes and the symptoms will decline in most cases within a day upon repeated application.

Hence, physiological liposomes are suited for the prophylactic and therapeutic treatment of eye diseases of allergic or viral etilogy, for instance;

conjunctival phlyctena belpharitis chemosis dacryoadenitis episcleritis, scleritis and tenonitis herpes corneae, herpex simplex of the lids and herpes zoster opthalmicus iritis and iridocyclitis keratitis conjunctivitis, such as c. follicular, c. allergica, c. epidermica, c. vernalis, inclusion blennorrhoea, and swimming-pool conjunctivitis molluscum contagiosum ophthalmia sympathica Since bile acids have an antibacterial effect, the cholate liposomes of the invention also exhibit bactericidal effects, at least against cholate-sensitive bacteria; i.e., some infections of bacterial etiolgy can also be treated in the case of the above-mentioned diseases.

Physiological liposomes can also be used against the following symptoms because of the regeneration-supporting and protecting effects:

dry-eye symptoms filamentary keratitis irritations caused by acid burns, burns, radiations and after surgical interventions keratoconjunctivitis sicca Sjögren's syndrome Stevens-Johnson syndrome contact lens intolerances because of the above-mentioned causes An addition of nutrients or mucoproteins to the liposomes may turn out to be more efficient in the case of especially serious symptoms. Physiological liposomes loaded with antioxidative substances such as vitamin C could perhaps be applied as a prophylactic against specific forms of the grey cataract (e.g. cataracta senilis).

V. Use of the physiological liposomes of the invention for the prophylactic and therapeutic treatment of inflammations and tissue lesions The liposomes of the invention can also be applied locally and systemically as an antiphlogistic agent and as a remedy against cell and tissue lesions.

As already depicted in sections II and III, one of the main working mechanisms of physiological liposomes is probably the inhibition of the mediator release and the neutralization of released mediators. The increased effect by vitamin C-containing liposomes points to pathological effects of oxidizing substances in these processes. Recently, more and more importance has been attached to oxygen radicals (5). The most important representatives of these radicals are the superoxide radical anion, the hydroxyl radical, alkoxy radicals and peroxy radicals. However, non-radical species such as singlet oxygen, organic peroxides and hydrogen peroxide, as well as hypochlorous acid, chlorine and chloramines which are biologically created from reactive oxygen species are also of pathogenetic relevance. These highly reactive substances are obtained during normal physiological processes and increasingly as antimicrobial resistance of specific immune cells. To protect themselves, the cells have various enzymes, of which the superoxide dismutase and catalase are probably the most important ones. Apart from this, vitamins E, C and A also act as antioxidants. The two extremely effective enzymes, however, are almost exclusively present in intracellular form whereas the extracellular or intercellular space into which polymorphonuclear leukocytes, monocytes and macrophages release the reactive oxygen species is almost entirely free from corresponding detoxifying mechanisms. These highly reactive substances damage not only the microorganisms which have penetrated thereinto, but also own tissue. Hence, the following processes take place in the subcellular structure:

depolymerization of collagens, proteoglycans, and hyaluronic acid decomposition of lipids denaturation of enzymes inactivation of serine protease inhibitors ($\alpha_1$-antitrypsin)

formation of leucotactic factors by interaction with metabolites of the arachidonic acid.

The following effects may play an important role in inflammatory processes as impacts on cellular structures;

(self-)destruction of leucocytes increase in vascular permeability erythrocytic lysis caused by damage to membrane lipids.

Of particular importance are the leucotactic factors which recruit further phagocytes to the place of inflammation, thereby further increasing the amount of reactive oxygen species. Interleukin (8) is considered to be of decisive importance to the first recruitment of phagocytes in the damaged tissue. Leukotrine $B_4$ and the activated complement component C5a, the most important one of the three anaphylatoxins (C3a, C4a, C5a), then serve as further chemotactic mediators. The extremely high efficiency of this chemotactic substance becomes apparent from the fact that a concentration of 1 to 5 nM leads already to a recruitment of the polymorphonuclear leucocytes (5). An activation of the leucocytes which leads to a release of lysosomal enzymes and the formation of other reactive oxygen species takes place simultaneously with this chemotaxis. Since C5a also acts on the vascular endotheliums, there will be a leucocyte aggregation, leucocyte adherence to the endotheliums and finally passage through the vascular wall. Secondary mediators take also part here. C5a has a proaggregatory effect on blood platelets. The propagation of this process may be limited to local inflammation processes or, however, lead to a systemic anaphylatoxin formation ending in a life-threatening shock. The processes which may lead to a systemic complement activation with anaphylatoxin formation include: endotoxinemia, bacteremia, polytraumata, burn, immune complex allergy, hemodialysis, leucopheresis, cardiopulmonary bypass and radiographic contrast media. A syndrome triggered by the systemic anaphlyatoxin formation is the shock lung ("adult respiratory distress syndrome") in which it is not only the aggregation of the leucocytes, but also their activation connected with the occurrence of reactive oxygen species and the occurrence of secondary mediators from the arachidonic acid cascade that play a role pathogenetically. The participation of anaphlyatoxins in local inflammations pressuposes a complement activation in the tissue or in the interstitial fluid. The presence of complement components in the lymph and the extravasation of plasma into the tissue by means of other inflammation mediators are suggestive of a local complement activation and thus of an anaphylatoxin participation in local inflammation processes. C5a was detected in synovial fluid of rheumatic patients, inflammatory exudates, in vessels with immunologically caused inflammations and also in liquor cerebrospinalis in the case of meningitis (5). For instance, the leukocytic infiltration in the case of such inflammations may be based on the chemotactic effect of C5a which, in turn, causes tissue damage through the activation of polymorphonuclear leucocytes by release of lyposomal enzymes (e.g. leucocytic elastase) or the formation of reactive oxygen species. In very simple words, the following picture could be drawn: Foreign substances or noxae induce specific immune cells to release reactive oxygen species, C5a is formed, and other immune cells are recruited with release of even higher amounts of reactive oxygen species, etc. The reaction may right away start with the formation of C5a when a noxa has a correspondingly strong action, for instance a burn. An intervention at any point of this cascade could avoid the build-up of this reaction.

The therapeutic possibilities which follow from the knowledge about the reactive oxygen species are largely unused. One of the few approaches is the application of bovine superoxide dismutase (Peroxinor®). Although the immunogenic potential of this bovine SOD in man is relatively small on account of a pronounced homology with respect to the human enzyme, the therapy remains limited to local injections or infiltrations. Local or generalized allergic symptoms were here observed only rarely, but an intravasal application remains contraindicated. If sufficiently high tissue levels can be achieved by local application, therapeutic successes are achieved with SOD (e.g. in the case of osteoarthritis of the knee, rheumatoid arthritis, radiation cystitis, interstitial cystitis and induratio penis plastica). Since a short time a human superoxide dismutase has been offered whose use will certainly enlarge the therapeutic spectrum. Of interest are here findings in the gerontological field according to which, at least in the animal model, there are correlations between especially long-lived culture strains of *Drosophila melanogaster* or through caenorhabditis elegans and its enzyme superoxide dismutase, the enzyme being present either in an especially active form or higher quantity. These findings support the presently favored aging theory according to which the permanent formation of potentially toxic, oxidative substances leads to an accumulation of irreversible damage (oxidized lipids, proteins, and DNS) in cells and tissues (8).

The antiphlogistic effect of physiological liposomes, especially with addition of vitamin C, becomes evident in the treatment of superficial burn injuries. When physiological liposomes are applied to the affected skin area immediately upon the action of heat, this will lead to a rapid pain reduction. When the application is repeated several times in the subsequent days, there will be no eruption of blisters and the tissue located below the destroyed skin will regenerate substantially faster and (also in the case of sensitive skin types) without the formation of scars. When blisters have already erupted, the application of physiological liposomes will lead to a drying up of the bubbles within a few hours. Hence, the liposomes suppress not only the extravasation of plasm into the tissue, but also guarantee an active return of fluid into the vessels. Similar restoring effects were observed after excessive impact of ultraviolet light (sun burn).

Inflammations have many things in common with allergic reactions. Since physiological liposomes effect a suppression of the mediator release and/or neutralization of released mediators as shown in section II, they are also suited for fighting inflammatory processes. Since oxygen radicals possibly play a more important role than in the case of allergies, an extra addition of antioxidative substances, such as vitamin C or urate, is of special benefit (also some of the liposome membrane-forming lipids have an antioxidative or reducing effect). In contrast to the above-described therapy with the enzyme superoxide dismutase, physiological liposomes also penetrate into the tissue and are, in addition, fully compatible because the membrane-forming components are molecules as also occur naturally in the body. With an intravenous application, large amounts of physiological liposomes can infuse without damage. The human physiology is designed in time-limited form for a drastic rise in numerous fat particles, as proven by the large amount of chylomicrons in the plasma after a fat meal (diameter 100—100 nm; components: 85% triglycerides, 5% cholesterol, 2% protein).

Physiological liposomes are suited for the topic and systemic therapy of many diseases of the inflammatory type. Apart from the already mentioned ones, the following could be considered as possible therapeutic objectives: intoxications, damage during respiration with hyperbaric oxygen, side effects of drugs and postischemia syndrome. In case of shocks caused by endotoxins or microorganisms and in case of microbially infected major tissue lesions, a simultaneous treatment with antibiotics might be indicated. The special antioxidative effects, as well as the unique penetrating capacities into tissues also recommend physiological liposomes as a geriatric agent.

Model of action of physiological liposomes

The findings presented in the preceding chapters show that physiological liposomes have a cellular effect as well as an extracellular effect. The effects of the bile acids transmitted by the liposomes onto the cell membrane and/or of the derivatives thereof as well as the lipids are probably and predominantly responsible for the cellular reactions. Viruses are inhibited in the extracellular space by these liposomes. Moreover, liposomal lipids and liposomally encapsulated antioxidants react with radicals. How these effects are to be imagined physiologically will be described in the following text:

1. Cellular effects of physiological liposomes

Bile acids and/or their derivatives are incorporated into the plasma membrane by the interaction of liposomes with cells.

1a. The incorporated cholate increases the permeability of the membrane because of the reduced surface tension above all for $NA^+$ (as the smallest one of the ions which are of importance to the membrane potential). This will lead to a sligthly increased $Na^+$ inflow into the cell. Water follows the changed osmotic gradient and makes the cell swell until the inner pressure can withstand the influence. Moreover, cells within a tissue unit permit this swelling only to a very limited degree due to the cells adjacent thereto, i.e., only up to the size that is permitted by the intercellular space (30 nm on average). An increase in the cell diameter by about 1% can here roughly be expected. The swelling of the cells cannot be explained by the liposome volumes introduced into the cell after fusion, for in order to cope with this additional volume the cell would have to incorporate the more than hundredfold amount of liposomal membrane material, which cannot be imagined with a view to the cell physiology. This slight swelling means in vivo that the interstice decreases, which, in turn, makes it more difficult for substances (for instance, mediators) and particles (for instance viruses) to propagate. In accordance with the changed ion concentrations, the $Na^+$—$K^+$-ATPase (Na+ pump) will try under ATP consumption to re-establish the original conditions. Under normal conditions this pump process already needs about one third of the whole energy consumption of a cell (in electrically active nerve cells about two thirds (12)). Hence, the energy consumption and thus the total metabolism of a cell will presumably rise after interaction with physiological liposomes.

If the interaction of liposomes and cells corresponds to a fusion, the following events might take place: After fusion of the liposome membrane with the cell membrane, a membrane piece having a size of about 0.1 $\mu m^2$ and increased permeability is incorporated through a liposome having a diameter of about 200 nm into the cell membrane (500 $m^2$ outer membrane surface at a cell diameter of 12.6 $\mu m$). As a result of this "new membrane piece" having a size of 0.1 $\mu m^2$, there is an increase in the inflow and outflow of ions.

However, since lipids, and presumably above all surfactants, diffuse laterally within the lipid double membrane at a rate of 2 $\mu$m/sec (7), the liposomal membrane piece already starts to flow apart at the time of the fusion, i.e., liposomal and cellular membrane components are mixed, which rapidly leads to a decrease in the ion permeability at this place of the cell membrane. A propagation of the liposomal membrane components to three to four times the area (0.3 to 0.4 $\mu$m$^2$) might already lead to a substantial decline in the permeability (derived from experiments with liposomes having a lower cholate proportion). The high rate of lateral lipid diffusion of 2 $\mu$m/sec might therefore "seal" the orginally 0.1 $\mu$m$^2$-sized liposomal membrane piece in fractions of a second for the greatest part. It is not until an increased number of liposomes have fused with a cell that the surfactants introduced into the cell membrane lead to a change in permeability regarding the whole cell membrane. It can be shown in vitro that cells react negatively to a very short-time (15–30 min) offer of very high liposome concentrations. After a few hours, however, the cells will fully recover therefrom. This regeneration can, inter alia, be explained by the fact that 50% of the plasma membrane are internalized per hour (depending on the cell type) and that consequently half of the cell membrane is replaced every hour by membrane material from the interior of the cell. The proportion of the cell membrane in the total membrane material of a cell amounts to a few percent only (in a liver cell to about 2%). The original permeability of the cell membrane is therefore re-established within a relatively short period of time.

However, if high liposome concentrations are offered to the cells for a long time, they will no longer be able to regenerate.

1b. The permeability of the plasma membrane which is slightly increased after liposome fusion results in a slightly weaker membrane potential (10). With nerve cells or the branches thereof, this has the consequence that the membrane potential moves closer to the "firing level", whereby a lower action potential is produced after the impulse generation. First electrophysiological derivations on hippocampus neurones in vitro show (own resultats) that in the presence of physiological liposomes the membrane potential (−60 mV) is brought by about 40 mV to −56 mV. Since the release of the neurotransmitter depends on the level of the action potential, a lower impulse will be transmitted to the next cell (muscle or nerve cell). This means in the case of pain generation that the pain abates and will disappear entirely in case of a correspondingly lowered action potential. (The question whether the tonic pain which is responsive to physiological liposomes is already based on a membrane potential of the participating cells which differs from the normal state and whether this will only be normalized again by the action of the liposomes cannot be answered at the moment). If the mediator release in immune cells (e.g. mast cells) also depends on the membrane potential and the granulate release of these cells is similar to the vesicle release at the synapses, the above-given explanation could also apply to some of the antiallergic and antiphlogistic properties of physiological liposomes.

1c. As a result of the cholate molecules introduced after fusion, the cell membrane becomes "liquid" because of the reduced surface tension. Cell surface structures depending on their spatial arrangement, such as the "coated pits" or IgE receptor aggregates caused by antigen binding, could be "loosened" by cholate. This would impede both virus binding and mast cell degranulation. Moreover, the complicated spatial arrangement of the transmembrane segments of the Na$^+$ channels (7) could be changed by the cholate molecules such that the effects described under 1b result therefrom. Furthermore, the spatial structure of receptors (for instance for histamine or opiates) and the assignment thereof to other membrane components, such as G proteins, adenylate cyclase, phospholipase C, protein kinase C and voltage-dependent ion channels are influenced by cholate such that this results in changed values of corresponding "second messengers" (for instance cAMP, DAG, IP$_3$, CA$^{2+}$).

2. Cellular and extracellular effects of physiological liposomes

The mono- or polyunsaturated fatty acids which are present in the liposome membrane, as well as other, additionally encapsulated antioxidants and reductants help to repair damage already caused by oxidative processes and to check the damage caused by newly formed radicals.

As described in sections I–V, the addition of vitamin C shows an intensifying effect of physiological liposomes although a reducing effect can evidently not be seen. Apart from other influences (see 10), this might be due to the following additional characteristics of vitamin C. A significant amount of vitamin C can be found within the liposomal lipid bilayer. The ascorbic acid may have an influence on the surface tension and thus also on the permeability of the membrane. For instance, vitamin C could be active not only through reduction, but also synergistically with respect to the surfactants of the liposome membrane (as in 1a and 1b). This permeability-influencing effect could also be caused by other substances, such as e.g. specific peptides.

3. Extracellualr effects of physiological liposomes

Physiological liposomes of a specific concentration forces viruses to interact with them, which leads to a viral inactivation. The surfactants existing in the liposomes presumably contribute considerably to the inactivation of viruses.

The following examples and figures will explain the invention.

A BRIEF DESCRIPTION OF THE DRAWINGS

FIG. 1A shows the time dependence of the inhibiting capacity of physiological liposomes on herpes simplex type I viruses with reference to infected vero cells.

FIG. 1B graphically illustrates the results shown in FIG. 1A.

FIG. 2A shows the dependence of the inhibiting capacity of physiological liposomes on the concentration thereof with reference to vero cells infected with herpex simplex type I viruses.

FIG. 2B graphically illustrates the results shown in FIG. 2A.

FIG. 3 shows the inhibiting capacity of physiological liposomes in response to the concentration of herpes simplex type I viruses of different concentrations.

Figure 5:
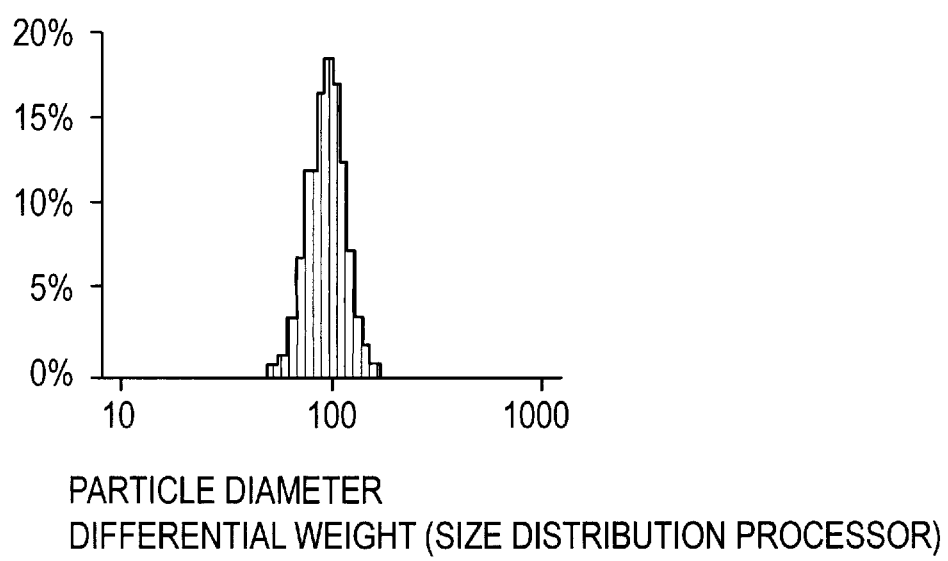

FIG. 5 graphically illustrates the size distribution of the liposomes used in Example 1.

FIG. 6 shows a comparison of earring tolerance with and without liposome treatment.

FIG. 7 shows the influence of the concentration of different liposomes on the concentration of isolated guinea pig intestine.

FIG. 8 graphically illustrates the densest packing that can be achieved in response to different virus diameters.

Figure 8A:
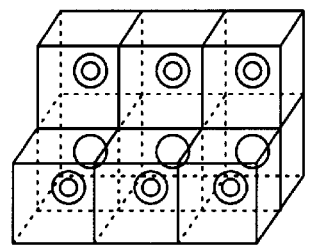

FIG. 8A starts from a virus diameter of 120 nm; a packing is reached at $10.9 \times 10^{13}$ liposome/ml.

Figure 8B:
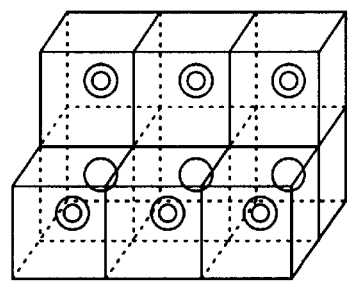

FIG. 8B starts from a virus diameter of 160 nm; a packing is reached at $6.5 \times 10^{13}$ liposome/ml.

Figure 8C:
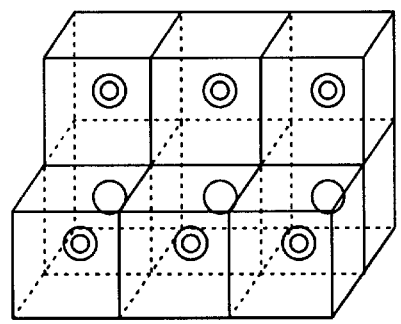

FIG. 8C starts from a virus diameter of 200 nm; a packing is reached at $4.2 \times 10^{13}$ liposome/ml.

EXAMPLE 1

Virustatic effect of physiological liposomes in vitro with reference to herpes simplex type I virus Experiment 1

About 420 PFU (plaque forming units) of a fresh isolate of herpes simplex type 1 (1.2 ml) were incubated for different periods with a liposome suspension (1.2 ml) which contained $7.3 \times 10^{13}$ liposomes per ml—unilamellar liposomes for the most part—after mixing. 3 g soybean lecithin were dissolved in 3 ml EtOH for preparing the liposomes. 3 g of sodium ascorbate, 0.27 g of common salt and 0.4 g of sodium cholate were dissolved in 23 ml double distilled water. The two solutions were well mixed by stirring, and the heterogenous mixture was sterilized by filtration at $5 \times 10^6$ Pa. The resultant liposome dispersion was adjusted to pH 6.8 with 1N hydrochloric acid and diluted to the necessary test concentrations. The virus-liposome mixture was then added to a confluent monolayer of monkey kidney cells of the vero type for 15 minutes and subsequently replaced by medium. The evaluation of the PFU created by the lytic viruses was done after 72 hours. The results of the tests are shown in FIGS. 1a and 1b. The control was applied for time O, i.e., viruses were added to the cells without liposomes. 420 PFU were measured after 3 days, which was equated with 100% PFU in the Fig. When the viruses were pipetted together with the liposomes and then immediately given to the cells, one only found 47% of the PFU in comparison with the control. This period of interaction of the liposomes with the viruses is about half a minute. After an incubation of the viruses with the liposomes for 10 minutes, only 26% PFU remained while less than 1% of the PFU could be detected after 30 minutes. About half of the viruses are directly inactivated after contact with the liposomes while some viruses remain infectious in the liposome suspension up to 30 minutes. This could be due to the heterogeneous morphology of the virus envelopes.

Experiment 2

Figure 2B:
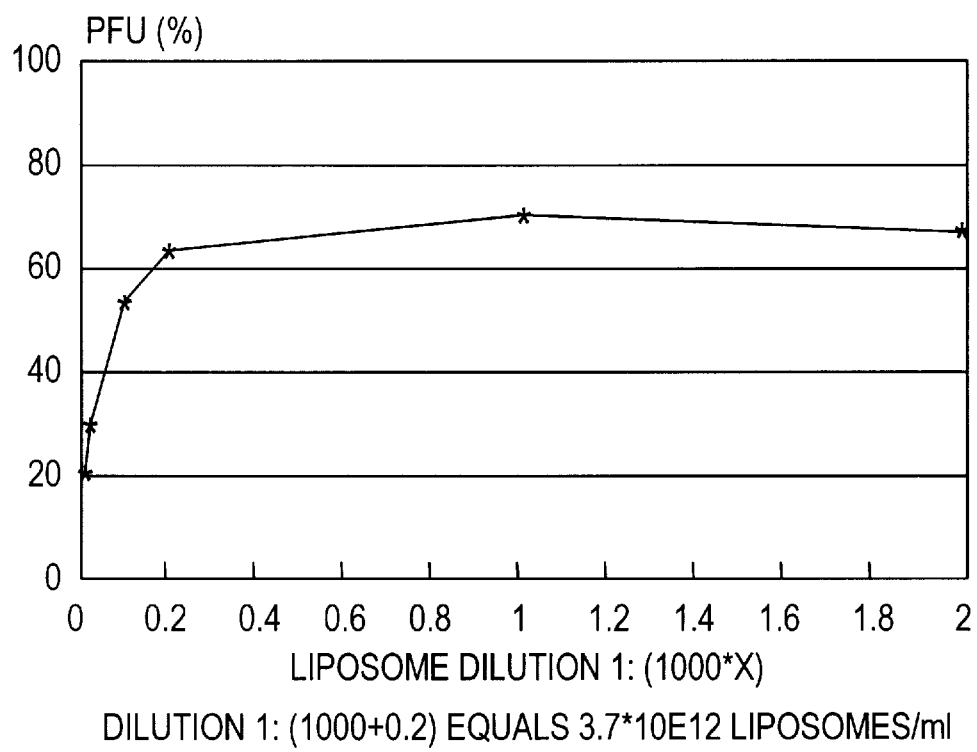

Different liposome concentrations (per 1.2 ml) were incubated with the same number of infectious viruses (140 PFU in 1.2 ml) in an incubator for 20 minutes and then offered to a veromonolayer for 15 minutes. The kinetics shown in FIGS. 2a and 2b follows from the percentage proportion of the PFU, based on the control without liposome addition. In the first dilution steps of $7.3 \times 10^{13}$ to $7.3 \times 10^{12}$ liposomes/ml, there is a pronounced decline in the inhibition efficiency of physiological liposomes. The virus inhibition remains constant between $3.7 \times 10^{12}$ and $3.7 \times 10^{11}$ liposomes/ml. The rapid decrease in the intensity of the inhibition in the first dilution steps and the unchanged inhibiting capacity in the case of incresaed dilutions point to two different mechanisms of action of physilogical liposomes.

Experiment 3

A mixture of one volume (1.2 ml) of liposome suspension ($1.4 \times 10^{14}$ liposomes/ml) and one volume (1.2 ml) of a virus dilution series ($10^{-2}$, $10^{-3}$, $10^{-4}$, $10^{-5}$) was prepared and incubated in an incubator at 36° C. Thereupon, it was applied to a vero cell monolayer: 0.5 ml of the mixture per plaque was respectively adsorbed in the incubator for 15 minutes, the inoculum was subsequently sucked off, once washed with PBS and then coated with 4 ml topagar. A mixture of virus plus PBS served as a control. After 3 days an assessment was made (FIG. 3). There is a pronounced virustatic effect in all virus dilution series. The difference between liposome-treated viruses (3 PFU) and the control (170 PFU) is more than factor 50 in the dilution step $10^{-4}$.

Experiment 4

Figure 4:
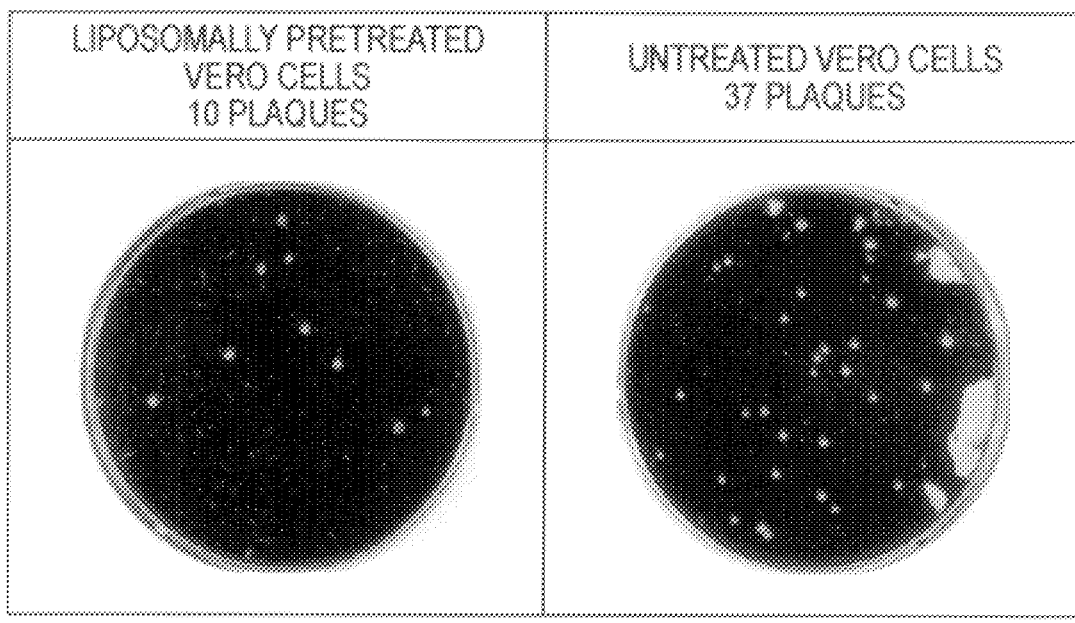
FIG. 4 shows the infection of a preincubation of vero cells with physiological liposomes in a subsequent incubation with herpes simplex type I viruses.

Confluent verocell monolayers were washed with PBS after the culture medium had been sucked off, and incubated with a suspension of $7.3 \times 10^{13}$ liposomes/ml in an incubator at 35° C. for 15 minutes. The liposome suspension was then sucked off and the cells were washed with PBS. Herpes viruses were plaque-titrated in the above-described manner on the verocell pretreated in this way. Vero cells which were not treated with liposomes served as a control. The result of this test is shown in FIG. 4. In comparison with the control, less than one third of the virus plaques were found on the pretreated vero cell monolayer after 3 days. One can drawn the conclusion therefrom that the interaction of the liposomes with the cell membrane leads to a certain "immunity" to the penetration of herpes viruses.

Evaluation of Example 1

The data obtained from experiments 1–4 point to two different inhibition mechanisms of physiological liposomes: On the one hand, there is an interaction—presumably in the form of a fusion—of the liposomes with the cells in such a manner that a subsequent virus contact leads to a successful infection only in one third of all cases (under the conditions here tested). This mechanism hardly depends on the liposome concentration. On the other hand, there is a virustatic effect through the interaction of the liposomes directly with the viruses, which effect depends greatly on the concentration of the liposomes.

On the basis of the almost complete inhibition of the herpes viruses in a liposome concentration of from $7.3 \times 10^{13}$/ml (Experiment 1) and the rapid decrease in inhibition in the case of slightly lower liposome concentrations (Experiment 2), there follows a relationship from the packing density of the liposomes and the size of the herpes viruses (diameter between 120 and 200 nm), which shall be shown in the following by way of a model:

A complete infection inbition is obtained due to physiological liposomes (r=45 nm) of the following concentration (with limit values under consideration of bi- and multilamellar liposomes, etc.; FIG. 5):

(minimum concentration: $5.0 \times 10^{13}$/ml)

mean concentration: $7.3 \times 10^{13}$/ml (maximum concentration: $12.0 \times 10^{13}$/ml)

Minimum value for the smallest virus size (see FIG. 8A)

herpes virus r=60 nm minimum liposome spacing: 120 nm maximum liposome spacing: 274 nm (spatial diagonal between 2 liposomes)

side length of cube: 210 nm capacity of cube: $9.2 \times 10^{-21}$ m$^3$ packing is reached at $10.9 \times 10^{13}$ liposomes/ml Average virus size (see FIG. 8B)

herpes virus r=80 nm
 minimum liposome spacing: 160 nm
 maximum liposome spacing: 343 nm
 side length of cube: 250 nm
 capacity of cube: $1.6 \times 10^{-20}$ m$^3$
 packing is reached at $6.4 \times 10^{13}$ liposomes/ml Maximum value for largest virus size (see FIG. 8C)

herpes virus r=100 nm
 minimum liposome spacing: 200 nm
 maximum liposome spacing: 412 nm
 side length of cube: 290 nm
 capacity of cube: $2.4 \times 10^{-20}$ m$^3$
 packing is obtained at $4.2 \times 10^{13}$ liposomes/ml In accordance with the present results, the most effective liposome concentration might be at about $7 \times 10^{13}$ liposomes/ml, depending on the incubation period and virus concentration. As for the calculated spacings, the model does not consider the interactions in the direct vicinity of the liposomes and viruses (hydrate envelopes, ion deposition, etc.) which might lead to an increase in spacing and thus to a lower effective liposome concentration. Moreover, since the forces are unknown which permit an interaction (fusion) of liposomes and herpes viruses after all, no definite information can be furnished about the model. If fusogenic proteins play no catalytic role in the interaction of liposomes and herpes viruses, one can assume that both particles must approach each other up to about 1.5 nm under displacement of the water molecule to permit a fusion. This is an energetically highly unfavorable process (12). This might only take place at a liposome density as is here the case. The good correspondence between the theoretical average value of $6.4 \times 10^{13}$ and the detected liposome concentration of $7.3 \times 10^{13}$/ml with an effect of almost 100% is here striking, as well as the correspondence of the rapid decrease in virus inhibition, which decrease can be forecast by the model, with the measured values at even slightly lower liposome concentrations. With a topic treatment of herpes patients, liposome concentrations of about $7 \times 10^{13}$/ml have turned out to be effective. An at least partial protection of the cells can also be achieved with lower liposome concentrations, as shown in Experiment 2.

EXAMPLE 2

Antiallergic effect of physiological liposomes with reference to earring intolerance Seven patients showing intolerance to earring of silver or base metals were treated with physiological liposomes. The application to the earlobe was performed once or repeatedly upon occurrence of renewed intolerance reactions. The patients were questioned after which time the first symptoms of an intolerance reaction showed up normally, i.e. without liposomal treatment. As becomes apparent from FIG. 6, there is a broad variance in the reaction to non-tolerated earrings. Moreover, the individual patients react differently to physiological liposomes. In an optimum case symptoms disappear after a single application for several weeks despite the wearing of otherwise intolerable jewelry. It can be inferred from numerically bigger studies that about 10% of the patients do not respond and 20% respond only to a limited degree while 70% respond to the treatment in a satisfactory to excellent manner.

Comparative tests with Tween® 20-containing liposomes did not show an alleviation of the symptoms.

EXAMPLE 3

Detection of membrane potential changes on the isolated intestine of guinea pig as caused by liposomes A piece of guinea pig ileum was electrically stimulated to contract in an organ bath, the intensity of the contractions were recorded and measured. Different concentrations of cholate-containing and surfactant-free liposomes (0.3 ml each) were added to the organ bath (25 ml buffer solution). The cholate-containing liposomes were prepared, as described in Experiment 1 of Example 1, while the surfactant-free liposomes were produced by treatment with ultrasonic waves of a lipid-containing, surfactant-free aqueous solution. As becomes apparent from FIG. 7, there is a huge difference in the effect of cholate-containing and surfactant-free liposomes. Cholate-containing liposomes (physiological liposomes) lead, in response to the concentration, to a decrease in the electrically stimulated intestinal contractions whereas the surfactant-free liposomes effect a considerable increase in the contraction.

EXAMPLE 4

Physiological liposomes for treating dry-eye symptoms

Twenty patients with dry-eye symptoms were treated with physiological liposomes over a period of 4 months. 12 patients then appeared for control tests. The subjective assessment by the patients was as follows:

considerable improvement: in 3 cases
 perceivable improvement: in 5 cases
 no improvement: in 4 cases It was found out in an objective follow-up examination of these 12 patients that the slit-lamp picture of the conjunctivae was more quiet in 9 cases than before the application of physiological liposomes. In the 8 cases of patients who did not appear for a follow-up examination, freedom from syptoms or therapeutic resignation can be assumed for the non-appearance.

EXAMPLE 5

Preparation of the liposomes of the invention 5 g of pure soybean lecithin are dissolved in 5 ml ethanol. 0.9 g sodium cholate is dissolved in 85 ml of a 0.9% saline solution. Both solutions are filtered at room temperature at $5 \times 10^6$ Pa through a filter with a pore size of 0.22 $\mu$m. The resultant liposomal solution contains liposomes with a mean diameter of 130 nm. The liposome solution obtained after single filtration can optionally be adjusted to the desired pH value.

We claim:

1. A method for reducing the intracellular ATP content in activated cells comprising the step of administering to a host a pharmaceutically effective amount of liposomes having an average mean diameter of 50–200 nm produced by a process comprising the steps of:

a) mixing i) bilayer-forming lipids or bilayer-forming lipids dissolved in a water-miscible solvent wherein said bilayer-forming lipids comprise unsaturated fatty-acid chains, with ii) an aqueous solution of at least one detergent selected from the group consisting of sodium cholate, sodium deoxycholate, sodium glycocholate, sodium taurocholate, sodium taurodeoxycholate, sodium ursocholate and sodium chenoxycholate at a molar ratio of lipid:detergent of 2.7:1–6.7:1 to form a mixture; and b) supplying mechanical energy until the liposomes are formed;

wherein the cells are activated by a process selected from the group consisting of:

i) transformation into tumor cells;
ii) intracellular amplification of viruses;
iii) contact with an allergen or antigen;
iv) contact with an inflammation causing agent;
v) agitation of nerve cells; and
vi) stimulation of the immune system;
and wherein said liposomes are free of drugs.

2. The method of claim 1, wherein said liposomes contain at least one antioxidant.

3. The method of claim 2, wherein said antioxidant is selected from the group consisting of BHA, BHT, octyl gallate, dodecyl gallate, sulfites, lactic acid, lactic acid salts, citric acid, citric acid salts, tartaric acid, tartaric acid salts, alpha-tocopherol, bilirubin, uric acid, and uric acid salts.

4. The method of claim 1, wherein said antioxidant is ascorbate.

5. A method for reducing the intracellular ATP content in activated cells comprising the step of administering to a host a pharmaceutically effective amount of liposomes having an average mean diameter of 50–200 nm consisting essentially of:
   i) at least one bilayer-forming lipid comprising unsaturated fatty-acid chains,
   ii) at least one substance selected from the group consisting of sodium cholate, sodium deoxycholate, sodium glycocholate, sodium taurocholate, sodium taurodeoxycholate, sodium ursocholate, and sodium chenoxycholate at a molar ratio of lipid:detergent of 2.7:1–6.7:1,
   iii) at least one alcohol having 2 to 6 carbon atoms, and
   iv) water or an aqueous solution of salts, with or without at least one additive selected from the group consisting of gel forming agents, buffer substances, membrane stabilizers, and preservatives;
   wherein the cells are activated by a process selected from the group consisting of:
   i) transformation into tumor cells;
   ii) intracellular amplification of viruses;
   iii) contact with an allergen or antigen;
   iv) contact with an inflammation causing agent;
   v) agitation of nerve cells; and
   vi) stimulation of the immune system.

6. The method of claim 5, wherein said liposome contains at least one antioxidant.

7. The method of claim 6, wherein said antioxidant is selected from the group consisting of BHA, BHT, octyl gallate, dodecyl gallate, sulfites, lactic acid, lactic acid salts, citric acid, citric acid salts, tartaric acid, tartaric acid salts, alpha-tocopherol, bilirubin, uric acid, and uric acid salts.

8. The method of claim 5, wherein said antioxidant is ascorbate.

9. A method for reducing the intracellular ATP content comprising the step of administering a pharmaceutically effective amount of liposomes having an average mean diameter of 50–200 nm produced by a process comprising the steps of:
   a) mixing i) bilayer-forming lipids or bilayer-forming lipids dissolved in a water-miscible solvent wherein said bilayer-forming lipids comprise unsaturated fatty-acid chains, with ii) an aqueous solution of at least one detergent selected from the group consisting of sodium cholate, sodium deoxycholate, sodium glycolate, sodium taurocholate, sodium taurodeoxycholate, sodium ursocholate and sodium chenoxycholate at a molar ratio of lipid:detergent of 2.7:1–6.7:1 to form a mixture; and
   b) supplying mechanical energy until the liposomes are formed;
   wherein said liposomes are free of drugs.

10. A method for reducing the intracellular ATP content comprising the step of administering a pharmaceutically effective amount of liposomes having an average mean diameter of 50–200 nm consisting essentially of:
   i) at least one bilayer-forming lipid comprising unsaturated fatty-acid chains,
   ii) at least one substance selected from the group consisting of sodium cholate, sodium deoxycholate, sodium glycocholate, sodium taurocholate, sodium taurodeoxycholate, sodium ursocholate, and sodium chenoxycholate at a molar ratio of lipid:detergent of 2.7:1–6.7:1,
   iii) at least one alcohol having 2 to 6 carbon atoms, and
   iv) water or an aqueous solution of salts, with or without at least one additive selected from the group consisting of gel forming agents, buffer substances, membrane stabilizers, and preservatives.

* * * * *

UNITED STATES PATENT AND TRADEMARK OFFICE
CERTIFICATE OF CORRECTION

PATENT NO.   : 5,853,753
DATED        : December 29, 1998
INVENTOR(S)  : Gunther Maierhofer, et al.

It is certified that error appears in the above-identified patent and that said Letters Patent is hereby corrected as shown below:

Replace FIG. 3 with FIG. 3 attached.

Signed and Sealed this

Twenty-first Day of December, 1999

*Attest:*

Q. TODD DICKINSON

*Attesting Officer*      *Acting Commissioner of Patents and Trademarks*

FIG. 3
| VIR. + LIPOS. VIR. DILUTION PLAQUE NO. | | VIR. CONTR. VIR. DILUTION PLAQUE NO. | |
|---|---|---|---|
| VIRUS DILUTION $10^{-5}$ 1 PLAQUE | 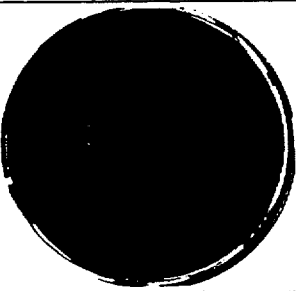 | VIRUS DILUTION $10^{-5}$ 14 PLAQUE | 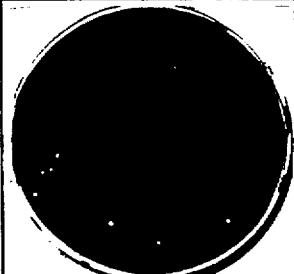 |
| VIRUS DILUTION $10^{-4}$ 3 PLAQUES | 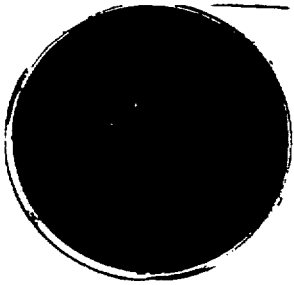 | VIRUS DILUTION $10^{-4}$ 170 PLAQUES | 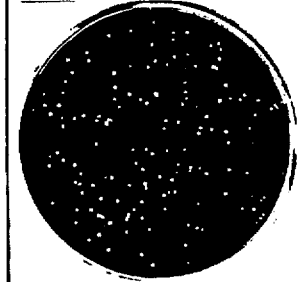 |
| VIRUS DILUTION $10^{-3}$ 101 PLAQUES | 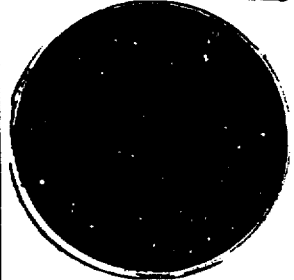 | VIRUS DILUTION $10^{-3}$ >500 PLAQUES | 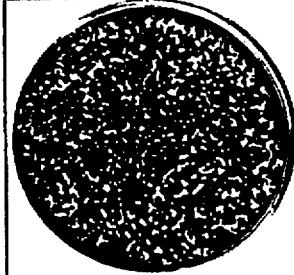 |
| VIRUS DILUTION $10^{-2}$ >500 PLAQUES | 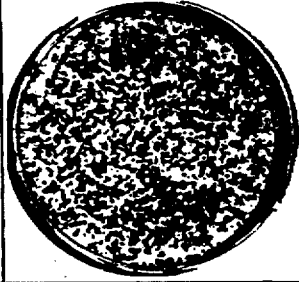 | VIRUS DILUTION $10^{-2}$ >>500 PLAQUES | 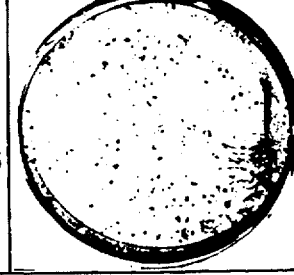 |